(12) United States Patent
Ramanathan

(10) Patent No.: US 11,925,769 B2
(45) Date of Patent: Mar. 12, 2024

(54) AORTIC VALVE NO EXCHANGE CATHETER AND METHODS OF USING THE SAME

(71) Applicant: ProMedica Health System, Inc., Toledo, OH (US)

(72) Inventor: P. Kasi Ramanathan, Ottawa Hills, OH (US)

(73) Assignee: PROMEDICA HEALTH SYSTEM, INC., Toledo, OH (US)

( * ) Notice: Subject to any disclaimer, the term of this patent is extended or adjusted under 35 U.S.C. 154(b) by 388 days.

(21) Appl. No.: 17/207,136

(22) Filed: Mar. 19, 2021

(65) Prior Publication Data

US 2021/0213247 A1 Jul. 15, 2021

Related U.S. Application Data

(63) Continuation of application No. 16/457,077, filed on Jun. 28, 2019, now Pat. No. 10,960,177.

(Continued)

(51) Int. Cl.
*A61M 25/00* (2006.01)
*A61M 5/00* (2006.01)
(Continued)

(52) U.S. Cl.
CPC ........ *A61M 25/0026* (2013.01); *A61M 5/007* (2013.01); *A61M 25/0108* (2013.01); *A61F 2/2436* (2013.01); *A61M 2025/0002* (2013.01); *A61M 2025/0003* (2013.01); *A61M 2025/0004* (2013.01); *A61M 25/0029* (2013.01); *A61M 25/003* (2013.01); *A61M 25/0041* (2013.01); *A61M 2025/0063* (2013.01);
(Continued)

(58) Field of Classification Search
CPC ............ A61M 25/0029; A61M 25/003; A61M 25/0136; A61M 25/0141; A61M 25/0026; A61M 25/0108; A61M 25/0041; A61M 25/0147; A61M 2025/0002; A61M 2025/0063; A61M 2025/0006; A61M 2025/0003; A61M 2025/0004; A61M 2025/0175; A61M 5/007; A61F 25/2427; A61F 25/2436; A62M 2230/30
See application file for complete search history.

(56) References Cited

U.S. PATENT DOCUMENTS 3,503,385 A 3/1970 Stevens
3,680,562 A 8/1972 Wittes et al.
(Continued)

*Primary Examiner* — Nathan R Price
*Assistant Examiner* — Tania Ismail
(74) *Attorney, Agent, or Firm* — Michael E. Dockins; Shumaker, Loop & Kendrick, LLP

(57) ABSTRACT

A medical device used to percutaneously gain access to a targeted site within a living body, for example the left ventricle of the heart. The device is comprised of an inner tubular member, outer tubular member, and an adjustable control handle. The control handle can precisely control the relative position of the inner tubular member relative to the outer member by providing feedback to the operator. This feedback provided by the control handle allows the operator to precisely maneuver the catheter within a body and change the shape of the catheter system without taking his/her eyes off the task that he/she is performing. The control handle is designed to precisely change the catheter system from one tip shape to another tip shape and back. Described herein are methods to use such devices.

19 Claims, 10 Drawing Sheets

Related U.S. Application Data

(60) Provisional application No. 62/692,222, filed on Jun. 29, 2018.

(51) Int. Cl.
*A61M 25/01* (2006.01)
*A61F 2/24* (2006.01)

(52) U.S. Cl.
CPC ..... *A61M 25/0136* (2013.01); *A61M 25/0141* (2013.01); *A61M 25/0147* (2013.01); *A61M 2025/0175* (2013.01); *A61M 2205/502* (2013.01); *A61M 2230/30* (2013.01)

(56) References Cited

U.S. PATENT DOCUMENTS

| | | |
|---|---|---|
| 4,033,331 A | 7/1977 | Guss et al. |
| 4,960,134 A | 10/1990 | Webster, Jr. |
| 5,120,323 A | 6/1992 | Shockey et al. |
| 5,666,970 A | 9/1997 | Smith |
| 6,190,360 B1 | 2/2001 | Iancea et al. |
| 10,532,193 B2 | 1/2020 | Fischer, Jr. et al. |
| 2007/0021732 A1 | 1/2007 | Hassett |
| 2011/0009699 A1 | 1/2011 | Slenker et al. |
| 2015/0119853 A1 | 4/2015 | Gainor et al. |

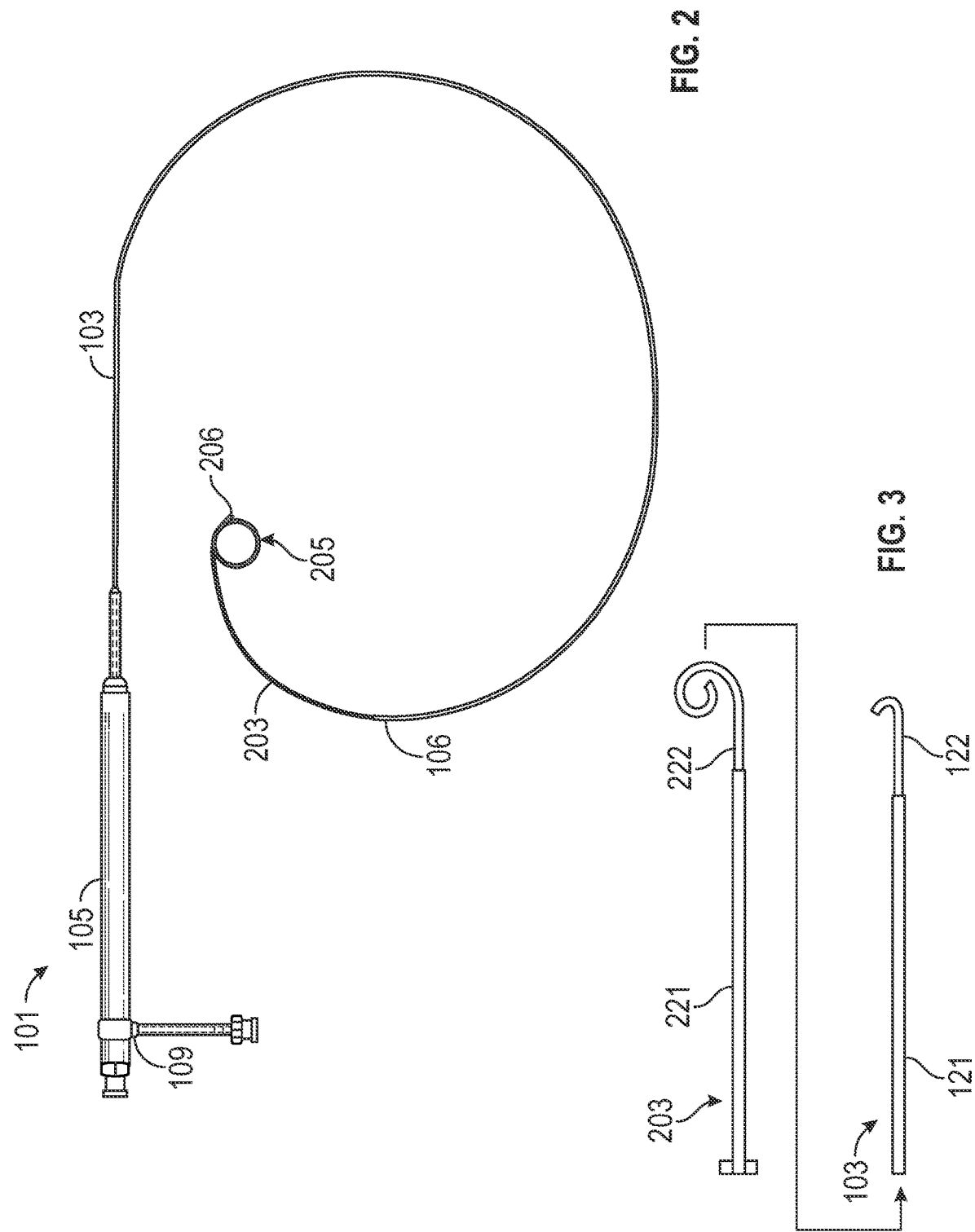

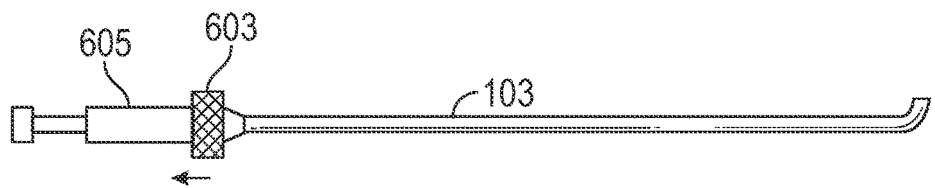
FIG. 5A
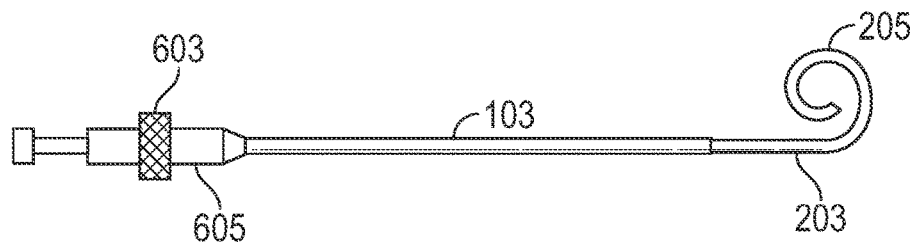
FIG. 5B
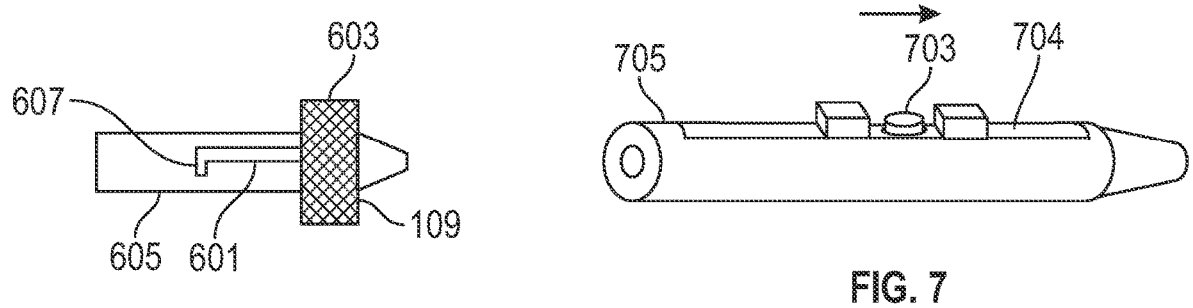
FIG. 6
FIG. 7
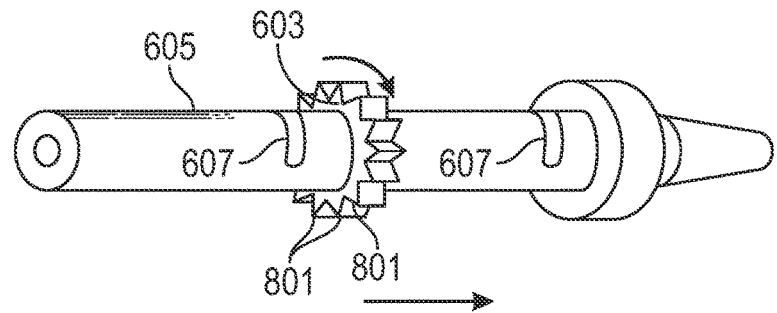
FIG. 8

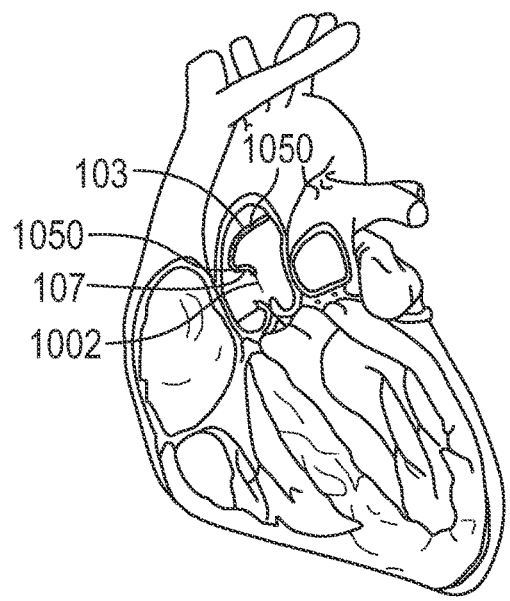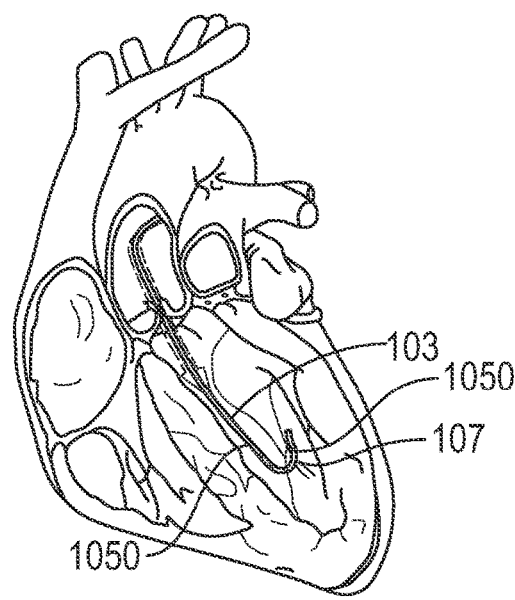
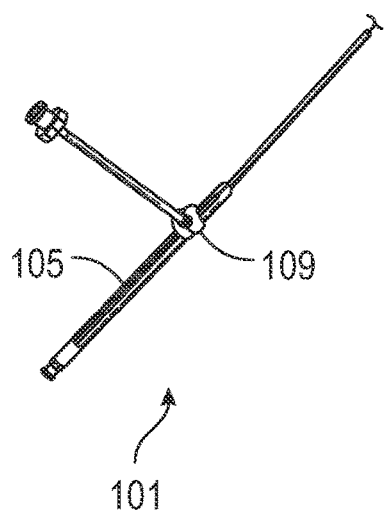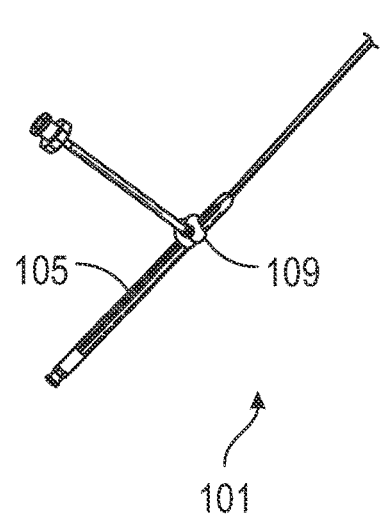
FIG. 10B                FIG. 10C

AORTIC VALVE NO EXCHANGE CATHETER AND METHODS OF USING THE SAME

CROSS-REFERENCE TO RELATED APPLICATIONS

This patent application is a continuation patent application of U.S. patent application Ser. No. 16/457,077 filed on Jun. 28, 2019, which claims the benefit of the benefit of U.S. Provisional Patent Application Ser. No. 62/692,222, filed on Jun. 29, 2018. The entire disclosure of the above application is incorporated herein by reference.

FIELD

The present technology relates to the field of devices used to gain vascular access to regions within a living body.

INTRODUCTION

While there are different methods to gain access to internal organs in the body to perform a medical procedure, less invasive approaches using catheters and guide wires delivered through the body's vascular system have become widespread. Minimally invasive procedures offer improved patient outcomes, often with fewer complications and shorter recovery periods. Consequently, increasingly complex interventional procedures have been developed to treat various diseases.

In treating heart disease, for example, the use of guide wires and catheters has a long-established history. Initially, percutaneous coronary interventions were often directed at diagnosing and treating blocked vessels within the heart. More recently, technologies to treat structural heart disorders have been developed and are now part of an interventionalist's armamentarium. Interventional structural heart technologies are comparatively complicated devices requiring advanced techniques to perform the procedure. For example, in transcatheter aortic valve replacement (TAVR) procedures (also known as percutaneous aortic valve replacement (PAVR) and as transcatheter aortic valve implantation (TAVI)), a prosthetic valve mounted on a stent is delivered via a catheter, over a guide wire, for placement over a patient's native valve apparatus.

The TAVR procedure is indicated for patients with severe aortic stenosis who may be intermediate or high risk for valve replacement surgery. The number of TAVR procedures has grown rapidly, year over year, as patients have chosen this minimally invasive approach over more traditional open chest, arrested heart procedures requiring a bypass pump. In order to perform a TAVR procedure, the interventionalist must first access the left ventricle.

Tools to gain access to the left ventricle exist, however, they are not ideal. There are numerous steps needed in a TAVR procedure prior to delivering the replacement valve. Developing improved technologies to combine needed steps can reduce procedural risks associated with multiple device exchanges. These risks include perforation of the heart or vessels and introduction of emboli resulting in stroke. There are other potential complications. The advanced techniques and the high level of concentration required to successfully perform a TAVR procedure highlights an unmet need to reduce device exchanges as much as possible to shorten and simplify the procedure in order improve patient outcomes.

In improving intravascular procedures, U.S. Pat. No. 3,503,385 to Stevens discloses a vascular diagnostic catheter with an embedded control wire, spanning from a catheter tip to a proximal (near) handle. A control mechanism attached to the handle manipulates the distal (far) tip of the catheter to form different curves. While this solution enables changing the shape of the distal end of a catheter, it is a costly solution that reduces space efficiency because of the need to have pull wires and the required lumens in a catheter shaft to house the pull wires.

U.S. Pat. No. 3,680,562 to Wittes et al. describes a catheter with an inwardly curved tip, like a pigtail, with a series of ports aligned longitudinally. A hollow piercing member is inserted to straighten the curved tip to facilitate delivery. There are other devices that similarly change shape using a stiff insertable member into the catheter. This device and others, which utilize a stiffening insert to change the shape of the distal end of the catheter, add steps to the procedure. The stiffening element must be inserted and withdrawn to achieve a shape change. In a complex procedure performed in a setting with many distractions, there is a need for the operator to be able to manipulate the catheter distal tip from an initial configuration to a final configuration quickly and easily, without taking undue attention and effort.

Pigtail shaped diagnostic catheters have long been used in intravascular medical procedures. They can be used to infuse imaging agents or drain fluid from organs. In addition, the pigtail configuration can be used to sheath a guide wire, offering protection against injury caused by a guide wire. The curved pigtail shape can have multiple loops which deflect the guide wire away from vulnerable tissue. Pigtail catheters, however, are not ideally shaped to traverse the vasculature to reach hard to access areas in the body. Pigtail catheters must often be exchanged with other guiding catheters more suitably shaped to reach a precise target location in the body. Making catheter exchanges often entails the need to exchange guide wires, further complicating the procedure.

U.S. Pat. No. 4,033,331 to Gus et al. describes the use of a wire to shape the tip of a catheter. The wire, which fills the internal lumen of the catheter, then must be extended or retracted to change the shape of the distal end. This method of catheter tip shaping can involve many steps. There is a need for a device which more efficiently reduces the steps needed to perform a procedure.

U.S. Pat. No. 5,120,323 to Shockey et al. discloses a telescoping guide catheter system comprised of an inner and outer guide catheter, neither of which is pre-curved. U.S. Pub. No. 2007/0021732 to Hassett describes an inner guiding introducer and an outer guiding introducer to access the left ventricle. Both the inner and outer members are pre-curved. However, both systems lack a means to precisely control retraction and extension of the inner member relative to the outer member.

U.S. Pat. No. 4,960,134 to Webster describes a catheter with a symmetrical cylindrical control handle and a flexible catheter tip. The control handle comprises a housing having a piston chamber. A piston is mounted in the piston chamber and can move lengthwise. The proximal end of the catheter body is fixedly attached to the distal end of the piston. A pull wire is attached to the housing and extends through to the catheter tip. Lengthwise movement of the piston relative to the housing results in deflection of the catheter tip. While a control mechanism enables precise tip deflection, the use of pull wires through a catheter using a dedicated lumen precludes a space efficient and cost effective solution.

U.S. Pat. No. 5,666,970 to Smith describes a control mechanism for manipulating the shape of the catheter and providing a rotational locking mechanism. This solution describes multiple moving elements, including a biasing member to control catheter movement. This complex solution requires a large housing, which makes it impractical to miniaturize and expensive to manufacture.

In U.S. Pub. No. 2015/0119853 to Gainor et al. describes a convertible shape catheter and method of use that includes the use of two catheters designed to work in tandem, one inside the other, to achieve any number of catheter distal tip shapes to advance through the anatomy and provide for a pigtail configuration. This unlimited range of adjustments becomes a hindrance in a procedure on a frail patient, where longer procedures are associated with serious complications such as renal failure due to the excessive use of imaging contrast and patient dehydration. For this design, catheter manipulation to change from an initial to a final orientation requires fluoroscopic visual guidance, with contrast media injections. This task may require a degree of operator concentration and extended manipulation that obviates any purported advantages.

The utilization of these prior art devices is highly limited. Their utility is compromised by size, complexity, difficulty of use, and cost. Consequently, there remains a need for a means to access a precise location within the body and provide an easy, controlled, and fast catheter shape change, in a cost and space efficient manner.

SUMMARY

The present technology relates to ways of using a catheter device to access a desired location within a body and effect a change to a distal tip shape of the catheter device, where the ability to change the distal tip shape can provide a shape optimal for insertion/withdrawal of the catheter device and a shape optimal for an intervention at the desired location.

Methods of using a concentric two-tube catheter device including an inner tubular member and an outer tubular member can include the following aspects. One of the inner tubular member and the outer tubular member is slidably disposed relative to the other one of the inner tubular member and the outer tubular member to expose a distal end of the inner tubular member from a distal end of the outer tubular member. The distal end of the outer tubular member can provide a first shape and the distal end of the inner tubular member can provide a second shape upon exposure thereof. The first shape and the second shape can be different.

The first shape and the second shape can vary in certain ways. The first shape can have less curvature than the second shape. The first shape can have a shorter curved length than the second shape. The first shape can include various standardized catheter tip shapes, including various Amplatz shapes and various Judkins shapes. Certain embodiments include where the second shape has a pigtail shape. The second shape can include where the distal end of the inner tubular member curves at least about 270 degrees from a remainder of the inner tubular member. Of the various paring options of the first shape and the second shape, a particular embodiment includes where the first shape has a hook shape and the second shape has a pigtail shape.

Various aspects of the inner tubular member and the outer tubular member can include the following. The outer tubular member can have a bending stiffness greater than a bending stiffness of the inner tubular member resulting in the second shape of the distal end of the inner tubular member conforming to the first shape of the distal end of the outer tubular member when the distal end of the inner tubular member is covered by the distal end of the outer tubular member. The inner tubular member can be slidably disposed to extend from the outer tubular member to expose the distal end of the inner tubular member from the distal end of the outer tubular member. Alternatively, the outer tubular member can be slidably disposed to retract from the outer tubular member to expose the distal end of the inner tubular member from the distal end of the outer tubular member. Slidably disposing one of the inner tubular member and the outer tubular member relative to the other one of the inner tubular member and the outer tubular member to expose the distal end of the inner tubular member from the distal end of the outer tubular member can include slidably disposing a control ring upon a handle body of the catheter device in a proximal to distal direction on the handle body to extend the inner tubular member relative to the outer tubular member and expose the distal end of the inner tubular member. Alternatively, slidably disposing one of the inner tubular member and the outer tubular member relative to the other one of the inner tubular member and the outer tubular member to expose the distal end of the inner tubular member from the distal end of the outer tubular member includes slidably disposing a control ring upon a handle body of the catheter device in a distal to proximal direction on the handle body to retract the outer tubular member relative to the inner tubular member and expose the distal end of the inner tubular member. It is also possible to lock the inner tubular member relative to the outer tubular member.

Other aspects of methods of using the concentric two-tube catheter device can include the following. Prior to slidably disposing one of the inner tubular member and the outer tubular member relative to the other one of the inner tubular member and the outer tubular member to expose a distal end of the inner tubular member from a distal end of the outer tubular member, the method can include extending a guide wire through the distal end of the inner tubular member. Methods can also include monitoring a pressure at the distal end of the inner tubular member and/or monitoring a pressure at the distal end of the outer tubular member. It is also possible to provide a fluid at the distal end of the inner tubular member, withdraw a fluid at the distal end of the inner tubular member, provide a fluid at the distal end of the outer tubular member, and/or withdraw a fluid at the distal end of the outer tubular member. Such methods can further include inflating a balloon at the distal end of the inner tubular member and/or inflating a balloon at the distal end of the outer tubular member. After slidably disposing one of the inner tubular member and the outer tubular member relative to the other one of the inner tubular member and the outer tubular member to expose a distal end of the inner tubular member from a distal end of the outer tubular member, the method can further comprise delivering and inflating a balloon using the catheter device, delivering a stent using the catheter device, and/or delivering a prosthetic valve using the catheter device.

Certain embodiments include methods of treating a heart of a patient using a concentric two-tube catheter device including an inner tubular member and an outer tubular member, where such methods include the following steps. The catheter device is advanced through an artery to the heart of the patient. A guide wire is extended through a distal end of the inner tubular member across an aortic valve of the heart of the patient. The catheter device is advanced into a ventricle of the heart of the heart of the patient. The outer tubular member is retracted relative to the inner tubular member to expose a distal end of the inner tubular member from a distal end of the outer tubular member, the distal end of the outer tubular member providing a first shape, the distal end of the inner tubular member providing a second shape upon exposure thereof, where the first shape and the second shape are different. Such methods can further include one or more of monitoring a pressure at the distal end of the inner tubular member, monitoring a pressure at the distal end of the outer tubular member, providing a fluid at the distal end of the inner tubular member, withdrawing a fluid at the distal end of the inner tubular member, providing a fluid at the distal end of the outer tubular member, withdrawing a fluid at the distal end of the outer tubular member, inflating a balloon at the distal end of the inner tubular member, inflating a balloon at the distal end of the outer tubular member, delivering and inflating a balloon using the catheter device, delivering a stent using the catheter device, and delivering a prosthetic valve using the catheter device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is an illustration of the catheter device with an inner tubular member forming a pigtail configuration at the distal end, extending from within the outer tubular member after manipulating the control handle to change the tip shape;

FIG. 3 is an exploded-view illustration of the inner and outer tubular members in component form shown separated for clarity;

FIG. 5A is an alternative embodiment of the catheter device in an initial configuration showing tip shape and handle position;

FIG. 5B is an alternative embodiment of the catheter device in a second configuration showing tip shape and handle position;

FIG. 6 is an illustration showing an alternative embodiment of a portion of the control handle;

FIG. 7 is an illustration showing an alternative embodiment of a control handle configuration with a spring-loaded detent system actuated by a depressible release button;

FIG. 8 is an illustration showing an alternative embodiment of a control handle with undulations on the outer surface of the circular control ring;

Figure 10A:
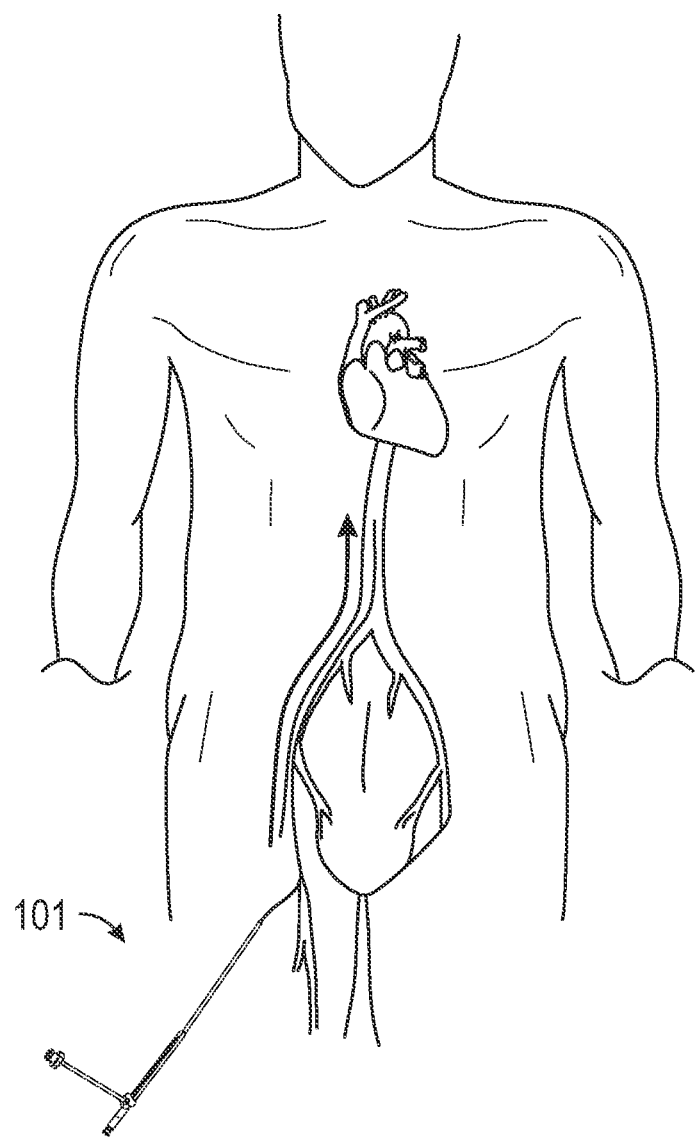
Figures 10D, 10E:
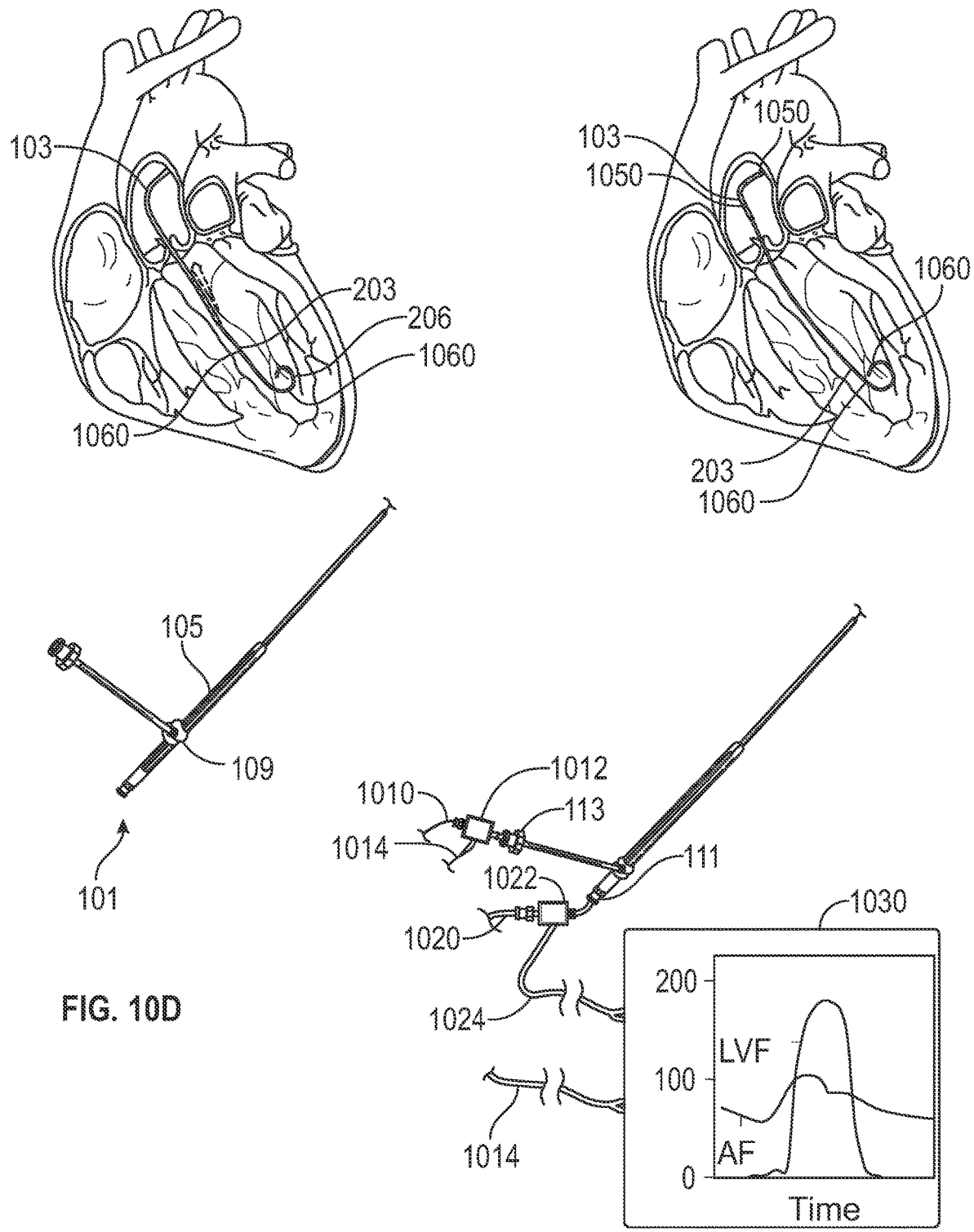
Figure 11:
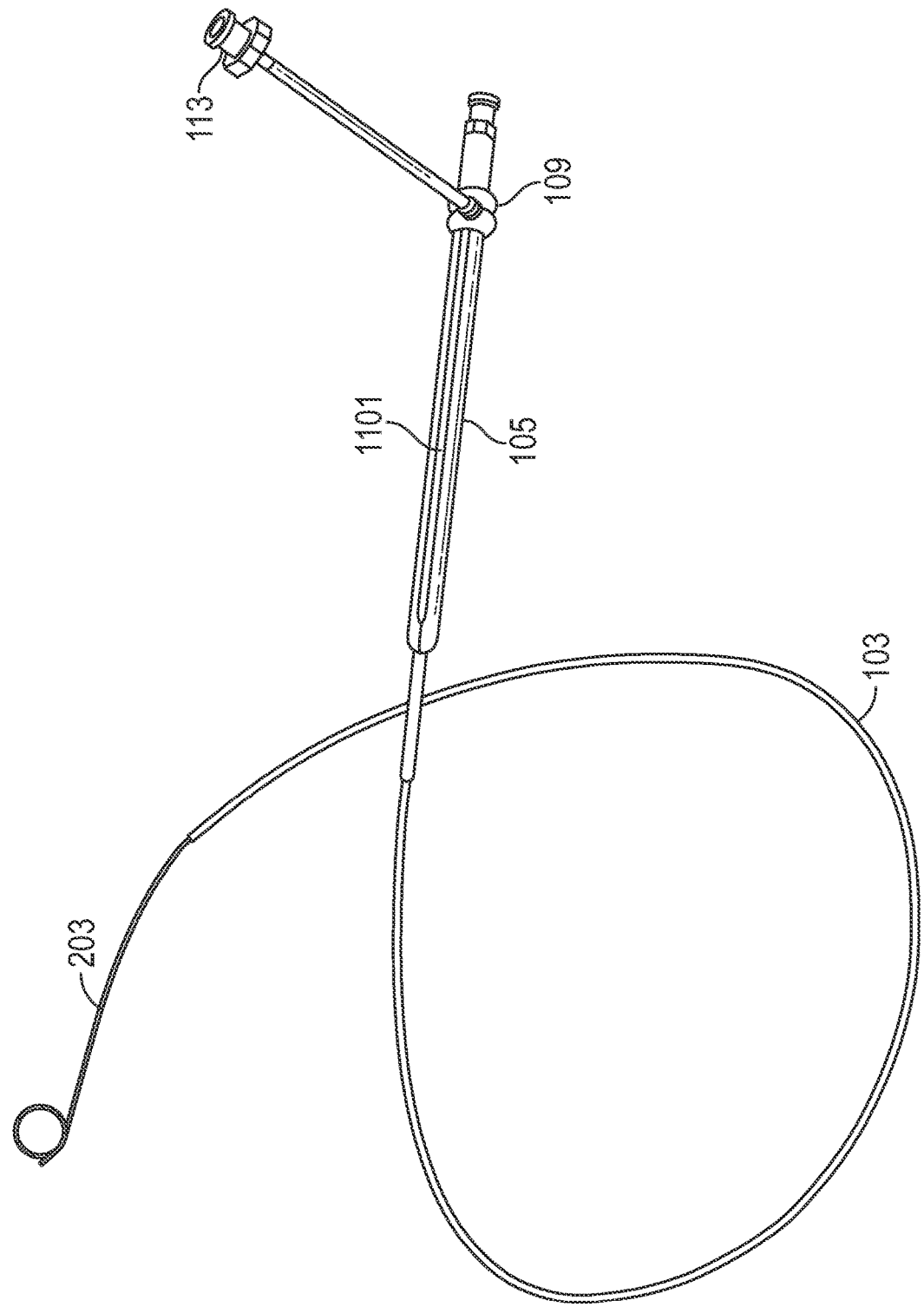
Figure 12:
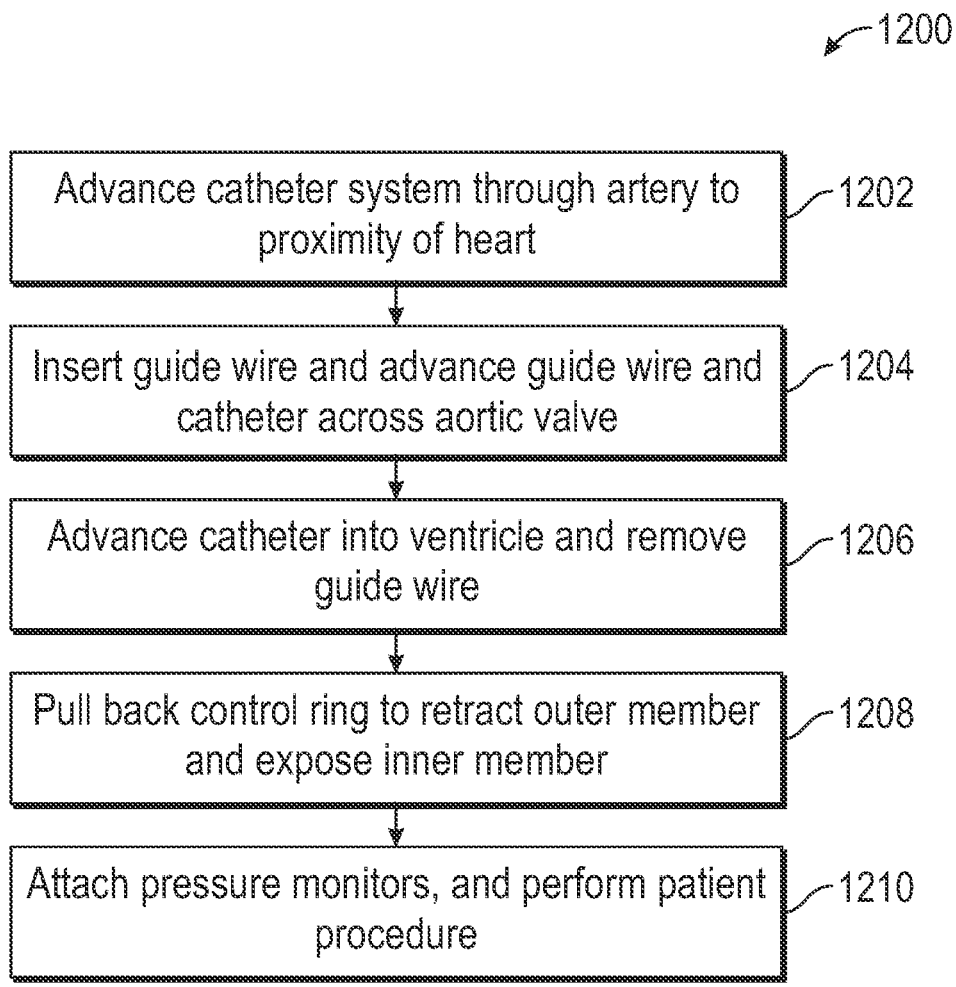

FIGS. 10A/B/C/D/E show the catheter device in the anatomy in various configurations;

FIG. 11 is an illustration of the catheter device shown with a view of the slot in the control handle mechanism that limits movement of the outer tubular member; and FIG. 12 is a flowchart diagram of a method for employing the disclosed catheter devices shown in FIGS. 1-11.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology provides ways to access one or more precise locations within a body of a patient using a catheter device and effect an easy and fast shape change at a distal end of the catheter device, thereby reducing a number of catheters and/or devices required for a given intervention, providing optimal control for an interventionalist, and simplifying an intervention procedure experienced by the patient. Methods of using a concentric two-tube catheter device including an inner tubular member and an outer tubular member are provided that include slidably disposing one of the inner tubular member and the outer tubular member relative to the other one of the inner tubular member and the outer tubular member to expose a distal end of the inner tubular member from a distal end of the outer tubular member. The distal end of the outer tubular member provides a first shape, the distal end of the inner tubular member provides a second shape upon exposure thereof, where the first shape and the second shape are different. For example, the first shape can have less curvature than the second shape and/or the first shape can have a shorter curved length than the second shape. The inner tubular member can be slidably disposed to extend from the outer tubular member to expose the distal end of the inner tubular member from the distal end of the outer tubular member and/or the outer tubular member can be slidably disposed to retract from the outer tubular member to expose the distal end of the inner tubular member from the distal end of the outer tubular member. In this way, the catheter device can be used to access a desired location within a body and effect a change to a distal tip shape of the catheter device, where the ability to change the distal tip shape can provide a shape optimal for insertion/withdrawal of the catheter device and a shape optimal for an intervention at the desired location.

The present technology can include aortic valve no exchange catheters and concentric two-tube catheter devices as described by U.S. patent application Ser. No. 15/907,456 to Ramanathan filed Feb. 28, 2018, which is incorporated herein by reference.

Examples of catheter systems and devices useful in performing the methods and procedures described herein can include the following structural features and functionalities. A catheter system can include an inner tubular member and an outer tubular member with an attached control handle mechanism. The inner tubular member and outer tubular member can also referred to as an inner catheter and an outer catheter. The outer tubular member can be advanced or retracted relative to the inner tubular member, the advancement or retraction controlled by a control handle mechanism. One or both of the inner tubular member and the outer tubular member can be pre-curved or, in other words, processed or configured to assume a non-linear shape. It is also possible that one or both of the inner tubular member and the outer tubular member can include one or more straight portions. The control handle can be designed to provide precise and repeatable movement of the outer tubular member relative to the inner tubular member. This can permit a change in catheter form and minimizes effort needed by an operator to make one or more changes to a shape of a distal portion of the catheter while performing a procedure.

The inner tubular member can have a resilience to adapt to a pre-curved shape of the outer tubular member when the outer tubular member is extended over a distal tip of the inner tubular member. This shape change feature can facilitate access to a treatment site, providing for an first configuration optimized to access the treatment site and a second configuration optimized for use at the treatment site. This system is designed to eliminate a catheter exchange and the need for multiple guide wire exchanges used to facilitate catheter exchanges.

The catheter device can include a relatively long inner tubular member as compared with the outer tubular member. The outer tubular member can be extended completely over the distal tip of the inner tubular member. The outer tubular member can be constructed with a stiffness that conforms the shape of the inner tubular member to that of the outer tubular member. The distal end of the outer tubular member can be shaped to optimize access to the left ventricle or another target site. A control handle can enable precise and repeatable movement of the outer tubular member resulting in a shape change from an initial tip shape configuration to a final tip shape configuration, by exposing the inner tubular member without distraction or undue manipulation. This can be accomplished by permitting a defined range of travel that can be governed by a distal stop, a movable range, and a proximal stop. This predefined range of motion can enable the operator to make tip shape changes easily and without the need for fluoroscopic visual confirmation and without the need for the operator to visually observe the handle when making a change.

The catheter device can also be configured to deliver one or more other devices into one or more other areas of the body, for example, into the left atrial chamber of the heart through a septal puncture, or into coronary arteries. More broadly, the catheter device can replace numerous devices needed to gain access to a specific location in the anatomy. The position of the control handle distal stop, allowable range of motion, and proximal stop are adjusted to suit a specific application. It can also be advantageous to reverse the direction of the catheter system movement, where instead of retracting the outer tubular member to expose the inner tubular member, to where the inner tubular member is extended past the end of the outer tubular member.

The control handle can precisely control the shape change of the catheter in repeatable manner. The range of motion of the outer tubular member can be constrained. This can be controlled by the allowable travel designed into the handle. In limiting the range of relative positioning, the operator can therefore facilitate a fast exchange, in a controlled manner, from a first configuration to a second configuration. A positive lock and/or detent mechanism can be incorporated into the control handle to secure the device in a desired configuration until the operator desires to change the catheter distal shape. The handle control mechanism can be optimized to provide a long range of movement in a small efficient package.

The outer tubular member can have a side port configured to fluidly communicate with the lumen of the outer tubular member. In this way, the lumen can be flushed with saline or other fluids. A vacuum can also be applied through the side port to remove air or other gas bubbles from the lumen of the outer tubular member to prevent air ingress into the blood circulation system.

A pressure transducer or a separate port engaged with a pressure transducer can be connected to the outer tubular member side port. The side port can have a threaded interface to ensure a secure and leak-free connection to other accessories. In other embodiments, the pressure sensor can be mounted near or at the distal end of the outer tubular member to make a more direct measurement of blood pressure. This can help overcome any deleterious dampening effects from trying to measure pressure through a small lumen in a catheter. In other words, the pressure signal can weaken over distance making the signal to noise ratio worse. In other embodiments, a dedicated lumen can be incorporated into a space between the outer tubular member and inner tubular member to provide a channel for blood to be in fluid communication with an external pressure sensor, where the dedicated lumen can reduce any pressure dampening effects that a small clearance between tubular members might create. In other embodiments, a micro-electronic mechanical (MEMs) pressure sensor can be integrated at the end of the outer tubular member to provide high fidelity pressure measurements.

An access port can be attached to a proximal most portion of the inner tubular member to enable delivery of other devices (e.g., one or more guide wires) or fluid (e.g., sterile saline). Alternatively, a pressure transducer and/or a separate port engaged with a pressure transducer can be connected to the proximal port. The proximal port described can have a threaded interface to ensure a secure and leak-free connection to other devices/accessories or to fluids.

The control handle can incorporate o-rings or other sealing means to seal the lumen of the outer catheter while still preserving its ability to be slid over the inner elongate tubular member. The O-rings or other sealing means can be incorporated into a housing that also serves to retract and, subsequently, advance the outer tubular member over the inner tubular member.

To enhance performance in certain embodiments, the control handle can be configured to retract the outer tubular member, rather than extend the inner tubular member. This operation can be provided to prevent undesired contact or injury within the left ventricle, for example. There are vulnerable structures, for example, such as papillary muscles, chordae tendineae, mitral valve leaflets, and other tissues or anatomical locations that can be damaged by inadvertent extension of the catheter.

Additional examples of catheter devices useful in performing the methods and procedures described herein can include the following structural features and functionalities. Concentric two-tube catheter devices can be employed where such devices include an inner tubular member, an outer tubular member, and a handle assembly. The inner tubular member can have a proximal end attached to a handle body and a distal end with a tip shape configured for a particular medical procedure. The outer tubular member can be concentric with and slidably disposed upon the inner tubular member, where the outer tubular member can have a proximal end attached to a control ring and a tip shape configured for placement of the catheter device in a patient. The handle assembly can include the handle body and the control ring, where the control ring can be slidably disposed upon the handle body. Positioning the control ring at a distal end of the handle body can cause the outer tubular member to be extended and cover the inner tubular member and positioning the control ring at a proximal end of the handle body can cause the outer tubular member to be retracted and expose the distal end of the inner tubular member. The outer tubular member can have a bending stiffness greater than that of the inner tubular member, where such causes the tip shape of the inner tubular member to conform to the tip shape of the outer tubular member when the inner tubular member is covered by the outer tubular member.

Such catheter devices can further include the following features and aspects. One or more side ports can be coupled to the control ring, where the side port(s) can be in fluid communication with an annular space between the outer tubular member and the inner tubular member. An end port can be coupled to a proximal end of the handle body that is in fluid communication with an interior of the inner tubular member. A first pressure transducer can be coupled to the end port, where the first pressure transducer can be configured to monitor a pressure at the distal end of the inner tubular member. A second pressure transducer coupled to a side port, where the second pressure transducer can be configured to monitor a pressure at the distal end of the outer tubular member. The first pressure transducer and the second pressure transducer can each provide a signal to a display device for visual display. A first fluid line can be coupled to the end port and/or a second fluid line can be coupled to the side port, where the first fluid line and the second fluid line are each configured to provide a fluid to, or withdraw fluids from, a distal end of the respective inner tubular member and outer tubular member. The inner tubular member and the end port can be configured to permit a guide wire to be inserted into the end port and advanced to and through the distal end of the inner tubular member.

In certain embodiments, a hypotube can be included that concentrically surrounds a proximal end of the inner tubular member inside the handle body. A flexible slider tube can couple the proximal end of the outer tubular member to the control ring, where the flexible slider tube concentrically surrounds and is slidable relative to the hypotube. The hypotube can be constructed of stainless steel, for example.

Catheter devices can further include where one or both of the inner tubular member and the outer tubular member has/have a plurality of holes formed through a tube wall near a distal end thereof. A slot can be provided in the handle body, where the slot is configured to define limits of travel of the control ring. A distal end of the slot can correspond to a control ring position that causes the outer tubular member to be extended to a position covering the distal end of the inner tubular member and a proximal end of the slot can correspond to a control ring position that retracts the outer tubular member and exposes a desired length of the distal end of the inner tubular member. A locking feature can be included in the handle body that allows locking the control ring in a position relative to the handle body. The locking feature can include a slot segment at each end of the slot, where the slot segments are oriented perpendicular to the slot and allow the control ring to be rotated into a locked position.

A radiopaque material can be provided in at least a portion of the inner tubular member and/or at least a portion of the outer tubular member, where the radiopaque material improves visibility of the respective portions of the catheter device under fluoroscopy or x-ray.

In certain embodiments, the inner tubular member and the outer tubular member each comprise a proximal segment and a distal segment, where each proximal segment has a greater bending stiffness than the respective distal segment. The tip shape of the outer tubular member can include a hook shape configured for advancing the outer tubular member to and across an aortic valve of a patient's heart. The tip shape of the inner tubular member can include a pigtail shape configured for performing a procedure in a ventricle of the heart.

The catheter systems and devices described herein can be used in various methods, including various treatments, surgical procedures, and interventions. Certain embodiments of such methods provide particular benefits and advantages in relation to the changing of a shape of a distal portion of a catheter device, including changing the shape of the distal portion of the catheter device located within a patient, such as within a blood vessel or an organ such as the heart. Such catheter devices can be used to overcome certain issues facing catheter insertion into a body cavity, duct, or vessel to treat a medial condition or disease or to perform a surgical procedure. In particular, there is an unmet need in interventional cardiology for percutaneous coronary intervention guide catheters that can access a portion of the vasculature in an optimal shape, and subsequently change to a more supportive configuration when the catheter arrives at the target vessel, in order to provide an advantage to the interventional cardiologist performing the procedure and thereby improve the procedure for the patient. For example, an interventional cardiologist may choose an aggressive or complex shaped guide catheter for percutaneous coronary intervention of the right coronary artery such as an AL1 guide; however, this aggressive or complex guide shape can lead to complications such as dissection of the right coronary artery or injury to the aorta. Finding a catheter that can optimally engage the ostium of the right coronary artery, but subsequently provide the support of an aggressive or complex shaped guide catheter such as the AL1 would be advantageous for both the interventionalist and the patient. Furthermore, in diagnostic catheterization, radial use has become more frequent due to less vascular complications.

A single catheter is often employed to minimize the number of catheter exchanges, which can reduce the risk of radial artery spasm. Catheters can be used to engage both the left and right coronary artery ostium for diagnostic angiography, but such catheters can employ aggressive or complex shapes and can lead to injury of the vessel. In clinical scenarios, including complex percutaneous coronary intervention and diagnostic radial catheterization, there is accordingly a need for catheters that can change shapes in an easy and seamless fashion when required, where the present technology provides catheter devices and uses thereof that can meet this need.

For complex percutaneous coronary intervention, an interventional cardiologist can be faced with choosing either an aggressive shaped guide catheter or use of another catheter within a catheter for additional support to deliver a stent. The present technology provides a solution to this problem. A guide catheter is provided that can have a standard shape to accurately engage the ostium of a coronary artery, where the catheter device is configured so that, if necessary, the interventionalist has the ability to advance a guide catheter that is 1 French size smaller further down the vessel. For example, for a complex percutaneous coronary intervention case, with a tortuous right coronary artery or a chronic total occlusion of the right coronary artery, the interventionalist may need to choose a guide catheter so that, if necessary, additional support can be provided.

The present technology therefore allows one to use a standard technique to engage the right coronary artery. If additional support is required, then one can advance a support catheter that is within the handle of the catheter device by advancing a sliding mechanism forward; e.g., where the handle can be advanced from a first or initial position to a second or final position. The mechanism of use for the present catheter device guide handle can be configured in a unique way, as rather than retracting the outer catheter, the inner catheter can be advanced. The handle can be advanced, for example, following introduction of a coronary wire (e.g., 014) through the coronary artery and across a stenosis. For further improvement, one can also advance a coronary balloon dilatation catheter down the wire, and then advance the guide extender (e.g., advancing the handle from a first or initial position to a second or final position) down the coronary artery. The guide extender can be contained in a compact fashion inside the small and compact handle. Furthermore, the guide handle can allow the guide extender to be housed in a compact fashion, and when extended, it can telescope out 10-20 cm, for example. With the 10 cm configuration, the handle can be smaller and more compact and can be ideal for a complex stenosis in the proximal to mid vessel. For a 20 cm extension configuration, the handle can be slightly larger in diameter to house the guide extender. In certain embodiments, the outer tubular member or outer catheter can be 1 French size larger than the inner tubular member or inner catheter; e.g., if the outer tubular member size is 6F, the inner tubular member size can be 5F. The handle can be extended and retracted as needed. The handle can include a locking mechanism to stay in a stable position so that if it is advanced only 7 cm of the total 10 cm, it can stay in that position. Furthermore, the inner tubular member or inner catheter can have a low pressure balloon that can be inflated to provide even greater support for the complex percutaneous coronary intervention procedure.

Advantages over existing guide extension catheters include the fact that the catheter device essentially includes an extending support catheter within it, minimizing the number of devices required. Furthermore, use of the present catheter device can be easier than introducing an additional catheter as the workflow is smoother for a physician as there is less equipment coming out of the backend of the catheter device. Furthermore, there are less exchanges and devices required with the present catheter device for complex percutaneous coronary intervention than with other devices.

The present technology further includes use of catheter devices in radial catheterization. Use of radial catheterization has increased for diagnostic catheterization in order to reduce complications associated with other techniques. For example, a single catheter is often employed to minimize the number of catheter exchanges, which can reduce the risk of radial artery spasm. Likewise, catheters exist to engage both the left and right coronary artery ostium for diagnostic angiography, but these have aggressive shapes and can lead to injury of the vessel. The present technology presents a solution to these problems, as a single catheter device is provided that can possess a standard JR and JL shape to optimally engage the ostium of the right coronary artery with the JR shape and the left coronary artery with the JL shape.

Embodiments of the present catheter devices and uses thereof include a combination of an inner tubular member (e.g., configured as 5F JR4 diagnostic catheter) and an outer tubular member (e.g., configured as a 6F JL4 diagnostic catheter). The inner tubular member can be contained within the outer tubular member, where the outer tubular member can be retracted using the handle mechanism, to thereby expose the inner tubular member (e.g., configured as 5F JR4 diagnostic catheter). One can use a 0.035 wire, for example, to advance the catheter device into the ascending aorta and then with the outer tubular member (e.g., configured as 6F JL4 diagnostic catheter) engage the left coronary artery. Once angiography is complete, one can remove the catheter device from the left coronary artery, and retract the outer tubular member to expose the inner tubular member (e.g., configured as 5F JR 4) using the handle. Once the inner tubular member (5F JR 4) is exposed, the inner tubular member can be used to engage the ostium of the right coronary artery. The handle structure and operation can be configured as the handle described herein and can operate in the same fashion. In certain embodiments, the catheter device does not need a pressure measuring port for the outer catheter.

The present technology further provides methods of accessing a target region of cardiac tissue, including the arteries and the major chambers of the heart. Such methods can include providing a medical instrument such as a catheter. Access to an artery in the body, such as the radial or femoral artery, is then created. A guide wire is inserted into the accessed artery and the guide wire is advanced from the access artery into a target region of the heart. A medical instrument, including a dual lumen catheter having inner and outer tubular members coaxially aligned substantially along a length of the catheter device, is extended over the guide wire so that the catheter device is advanced to the target region of the heart. The control handle is manipulated to extend or retract one of the tubular members so that the other tubular member is extended or exposed such that a proximal segment of the catheter is dual lumen and a distal segment is a single lumen catheter. The distal tip shape of the catheter device thereby changes from one configuration to a different configuration.

Examples

Example embodiments of the present technology are provided with reference to the several figures enclosed herewith.

Figure 1:
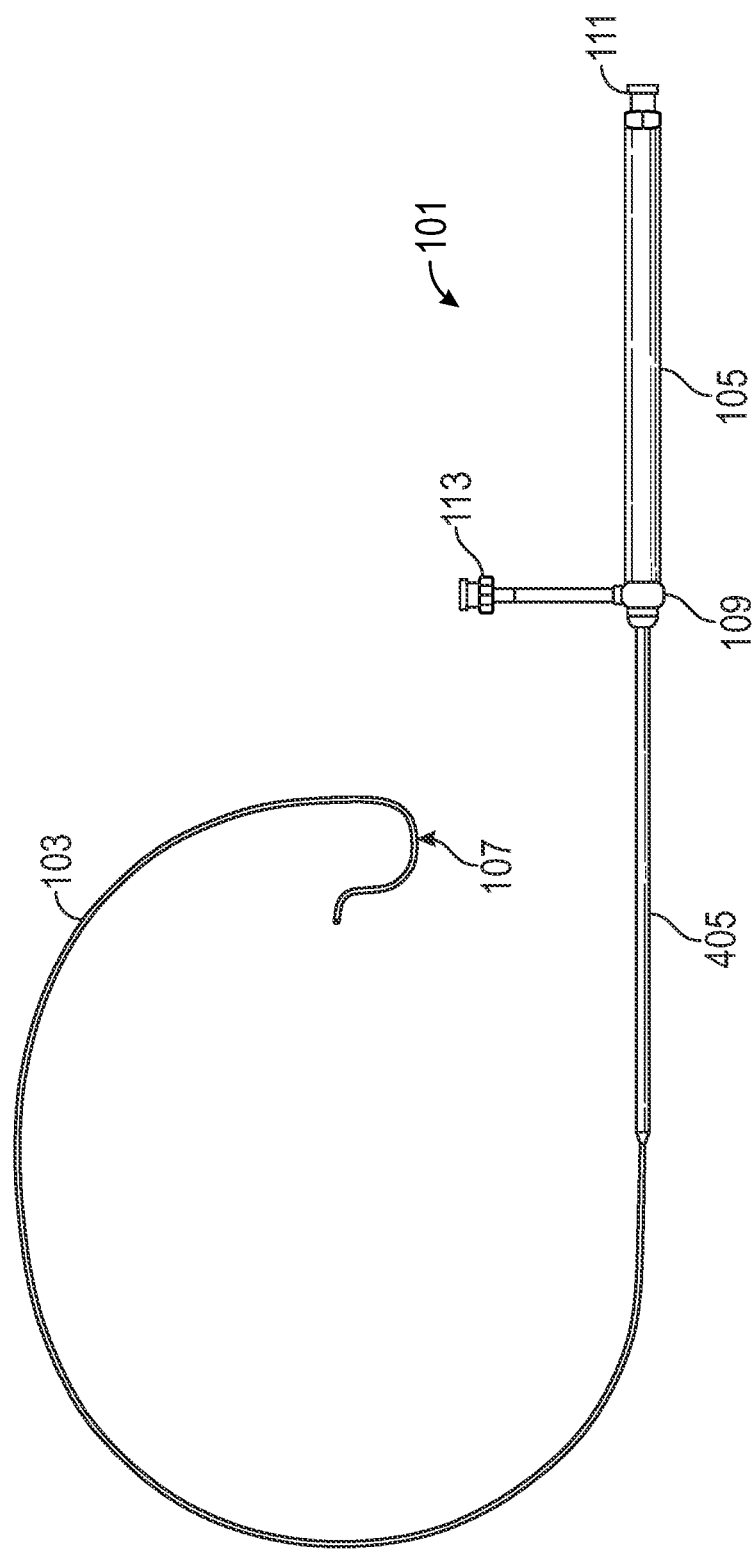
FIG. 1 is an illustration of a catheter device constructed in accordance with the present technology, where the catheter device is shown in its initial configuration with an outer tubular member in an AL1 catheter tip configuration.

With reference to FIG. 1, a no exchange catheter system 101 is shown that benefits by reducing the need to remove and exchange various catheters and guide wires during a medical procedure. Shown in FIG. 2 is the no exchange catheter system 101, comprised of an inner tubular member 203 within an outer tubular member 103 each attached to separate components of a control handle 105 approximately at their proximal ends. As discussed below, the outer tubular member 103 is slidably extensible and retractable over the inner tubular member 203, controlled by the components of the control handle 105.

The inner tubular member 203 is longer than the outer tubular member 103. In exemplary fashion, an inner tubular member 203 may have a pigtail shape 205 at its distal end 206, and may be "5F" (meaning 5 on the French scale, which equates to a diameter of 1.667 mm), and 110 cm long. The outer tubular member 103 may have an AL1 (a particular type of tip) shape at its distal end 107, and can be 6F (2 mm diameter), and is 90 cm long. Other lengths and diameters are contemplated. For example, the total catheter length can be 125 cm and the range of movement of the outer tubular member 103 over the inner tubular member 203 can be 12 cm. For transcatheter aortic valve replacement procedures, the standard guide wire length of 260 cm dictates the total catheter system length be less than 130 cm, and preferably close to 130 cm. Other tip shapes may also be used as best suited for a particular application.

The control handle 105, at the proximal end of the catheter system 101, has a circular control ring 109 to facilitate movement of the outer tubular member 103. When the operator pulls back the outer tubular member 103 via sliding the circular control ring 109 back on the control handle 105, the distal end of the inner tubular member 203 is exposed and forms a pigtail shape when fully extended from the outer tubular member 103. The linear range of motion of the outer tubular member 103 can be 10 to 20 cm. Other distal inner tubular member shapes are contemplated and can be similarly exposed when the outer tubular member 103 is retracted. Likewise, the range of linear travel for the outer tubular member 103 can be optimized for other contemplated applications such as converting a Judkins left catheter to a Judkins right catheter and utilizing a range of travel that is less than 10 cm. Alternatively, other applications may dictate a larger than 20 cm range of travel.

By design, the control handle 105 limits travel of the circular control ring 109 and thus the travel of the outer tubular member 103 over the inner tubular member 203. This is controlled in one embodiment by the dimensions of a slot 1101 in the control handle 105 as shown in FIG. 11. In some embodiments of the present technology, a control ring locking feature is used to temporarily fix the position of the outer tubular member 103 relative to the inner tubular member 203, where the catheter shape can be locked into position only when the outer tubular member 103 is fully extended or fully retracted. Referring to FIG. 6, a slot segment 607 extending 90 degrees from a longitudinal travel slot 601 is provided to immobilize a circular control ring 603 at the extreme limit of the circular control ring travel. The circular control ring 603 performs the same function as the circular control ring 109—that is, controls the position of the outer tubular member 103 relative to the inner tubular member 203. When at either of two extreme positions, the circular control ring 603 can be rotated to lock the position of the catheter. In FIG. 6, the control ring 603 covers another of the slot segments 607 which is at the distal end of the longitudinal slot 601. Alternatively, the slot 1101 of FIG. 11 or a hard stop (not shown) built into the handle can preclude axial movement, forward and backwards, in place of a twist lock mechanism.

The circular control ring 603 is shown in FIG. 6 as having a knurled outer surface. FIG. 8 shows a control ring with outward facing undulations 801 or other features designed to enhance grip for operators wearing gloves.

FIG. 1 depicts the device in the initial configuration, shown here as an Amplatzer AL1 tip shape. Alternatively, the shape of the distal segment may be that of an Amplatzer AL2 or any other shape an operator prefers to gain access to a particular area of the anatomy. The outer tubular member 103 has been extended to cover the distal end of the inner tubular member 203 (thus the inner tubular member 203 is not visible in FIG. 1), and the distal tips of the inner tubular member 203 and outer tubular member 203 are aligned. In this position, the distal shape of the catheter is governed by the shape of the outer tubular member 103. A luer 111 is fused to the proximal most edge of the inner tubular member 203, thereby allowing a fluidic coupling to the proximal end of the inner tubular member 203. The fluidic coupling provided by the luer 111 may be used to monitor pressure in the inner tubular member 203, or deliver a fluid through the inner tubular member 203, for example. In FIG. 1, the circular control ring 109 is in its distal most position, relative to the handle 105; this position of the circular control ring 109 is what causes the outer tubular member 103 to be fully extended over the inner tubular member 203.

A side port assembly 113 is attached to the circular control ring 109 and is able to fluidly communicate with the space between the inner tubular member 203 and the outer tubular member 103, regardless of the position of the circular control ring 109. The fluid communication space is sealed using O-rings or other sealing means, discussed below. The O-rings are designed to slide along with the circular control ring 109.

FIG. 2 depicts the device with the pigtail section 205 shown at the distal end 206 of the inner tubular member 203. In this configuration, the outer tubular member 103 has been fully retracted to expose the distal end of the inner tubular member 203. The inner tubular member 203 can be longer than the outer tubular member 103. Hence, in this configuration of FIG. 2, a section of the inner tubular member 203 is extended from the outer tubular member 103. The circular control ring 109 is in its proximal most position in this configuration, which is what caused the outer tubular member 103 to retract and expose the portion of the inner tubular member 203. A distal tip 106 of the outer tubular member 103 is denoted on FIG. 2; this is the point at which the inner tubular member 203 emerges from the outer tubular member 103.

FIG. 3 depicts the inner tubular member 203 and the outer tubular member 103 as separated, with each showing an exemplary tip shape. The inner tubular member 203 is made from a relatively flexible polymeric material, one that conforms to the shape of the outer tubular member 103 when inserted into the outer tubular member 103. The polymeric inner tubular member 203 is made from a soft material such as a thermoplastic elastomer. One such soft material is a polyether block amide and has a low durometer value, for example, 35-55 Shore D. An example of the polyether block amide is sold under the trademark PEBAX®. Other polymers such as thermoplastic polyurethanes with similar softness and similar durometer ranges are also contemplated. These materials are well known to those skilled in the art. The wall of the inner tubular member 203 is made deliberately thin, for example in a range of 0.003" to 0.007". The preferred wall thickness is approximately 0.005". The thin wall thickness facilitates shape conformance of the inner tubular member 203 to the outer tubular member 103.

The polymeric outer tubular member 103 is made from a relatively stiffer material than the inner tubular member 203. This can be accomplished using a higher durometer polymer, relative to the inner tubular member 203. A polymeric material such as a polyether block amide in a range of durometers such as 55-76 Shore D are suitable. An example of the polyether block amide is sold under the trademark PEBAX®. Other polymers such as thermoplastic polyurethanes with similar softness and similar durometer ranges are also contemplated.

The stiffness of the individual tubular members can be varied using one or more of several techniques including selecting and/or mixing polymers of differing hardness, adjusting the tubing wall thickness, incorporating a stainless steel braid reinforcement, and/or using a multi-layer tubing design.

Typical intravascular catheters can be comprised of two sections, namely a proximal and distal section. These two sections are fused together to form one complete catheter. However, each section is designed to perform a different function. For example, the first, or proximal section, tends to be straight and stiff to enable advancement of the catheter to a target region. The second, or distal section, is typically softer and shaped to engage the anatomy. It is a common practice to utilize different stiffness grades of the same basic polymer material to fabricate the proximal and distal segments of each tubular member.

The inner tubular member 203 of the present technology is comprised of a first section 221 and a second section 222, wherein the first section 221 is a generally elongated straight section which is connected at its distal end with the second section 222, which is a curved section such as a pigtail configuration.

Similarly, the outer tubular member 103 of the present technology is comprised of a first section 121 and a second section 122, wherein the first section 121 is a generally elongated straight section which is connected at its distal end with the second section 122 that forms a compound curve designed to easily access the aortic valve and provide passage to the left ventricle. An example of a distal shape may be an Amplatzer AL1.

Figure 4:
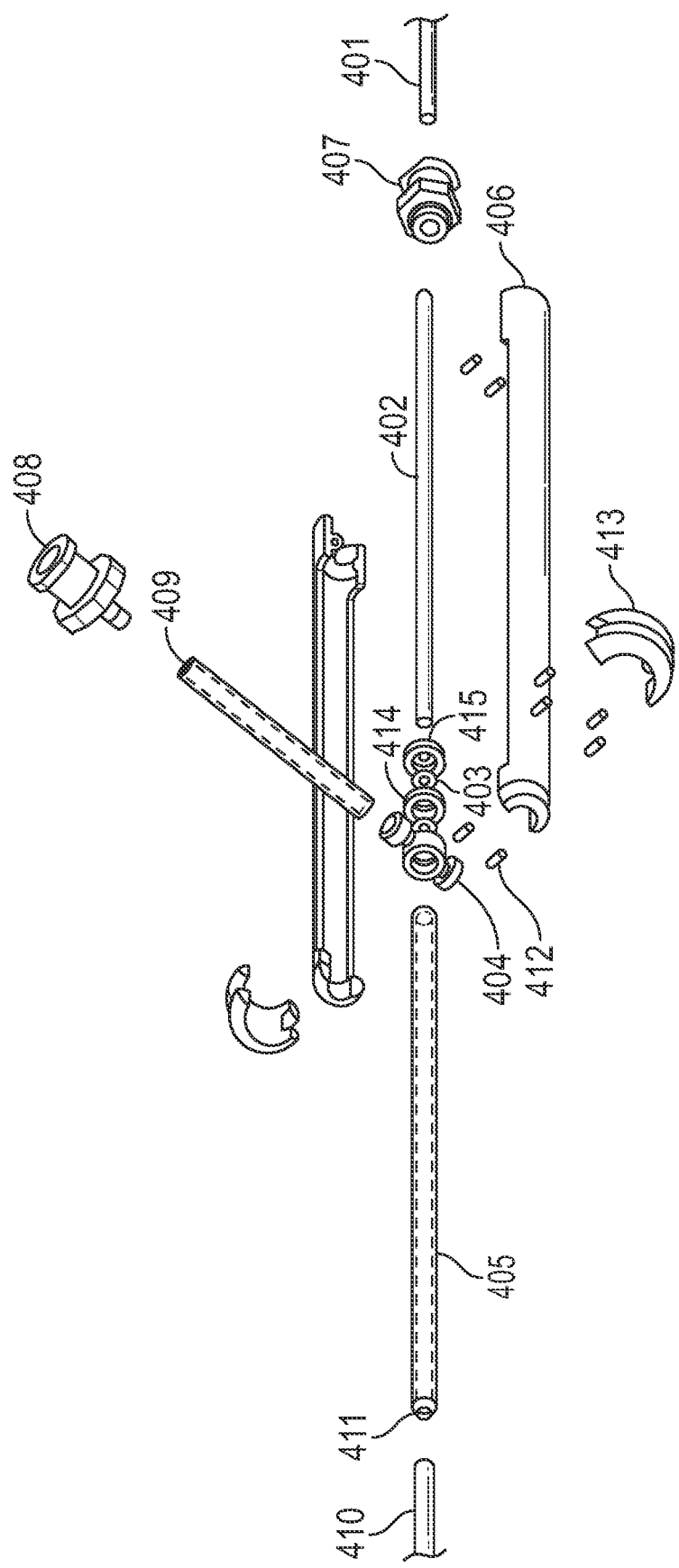
FIG. 4 is an exploded-view illustration of the control handle.

FIG. 4 shows the major components of the control handle assembly in an exploded view. In short, the handle assembly provides for a slidable and leak free outer tubular member 103 configured to slide over a reinforced inner tubular member 203. The outer tubular member 103 is attached to a control handle mechanism enabling the operator to retract or advance the outer tubular member 103. A distal end 401 of the inner tubular member 203 may be inserted through the handle components for assembly. A stainless steel hypotube 402 is inserted over the inner tubular member 203, is used to reinforce the inner tubular member 203, and functions to prevent unwanted bending or kinking of the inner tubular member 203 during handle manipulation.

A sealing means such as an O-ring, a plurality of O-rings, or a hemostasis valve, adapted for sliding along a stiff, reinforcing member enables relative movement of the inner tubular member 203 and outer tubular member 103 while continuously providing a blood hemostasis seal. O-rings 403 are used to seal the proximal most portion 410 of the outer tubular member 103, which in turn, is fused to a flexible slider tube 405. This ensures a leak free system enabling the inner tubular member 203 and the outer tubular member 103 to be slidable in relation to each other.

A main body 404 within the circular control ring houses the O-rings 403 and provides for a sealed fluid path (dashed line in FIG. 9) from the proximal segment 410 of the outer tubular member 103 to the side port 408. A flexible slider tube 405 is inserted into the proximal segment 410 of the outer tubular member 103. This enables the distal end 401 of the inner tubular member 203 and the stainless steel hypotube 402 to fit within the flexible slider tube 405. An adhesive bond with an adhesive fillet 411 provides a leak-free seal between the flexible slider tube 405 and the proximal segment 410 of the outer tubular member 103 after assembly.

The control handle mechanism housing 406 has a slot (FIG. 11, 1101) providing a fixed range of travel for the control ring 109. The control handle mechanism housing 406 is made in two halves, which when assembled are joined using adhesive or fasteners. The control handle mechanism housing 406 houses the distal end 401 of the inner tubular member 203 and provides the operator with a feature to grip the catheter. A luer 407 is bonded to the proximal end of the inner tubular member 203 and provides a means to couple the inner tubular member 203 to accessories such as a syringe or a Touhy Borst connector (not shown).

The circular control ring 413 (same as control ring 109) is assembled from two halves bonded together and provides the operator with an easy to grip surface to manipulate the position of the outer tubular member 103. The circular control ring 109 attaches to the handle control mechanism 105 as shown in FIG. 1. This assembly, in turn, houses O-rings 403, an O-ring slider mid-body 414, and O-ring slider end cap 415, and maintains the O-rings in position. Dowel pins 412 can be used to fasten the circular control ring halves 413 together immobilizing the components in the circular control ring 109. A side port tubing 409 connects the side port 408 to the proximal segment 410 of the outer tubular member 103, to enable a leak free fluid communication path from the side port 408 (or 113 in FIG. 1) to the outer tubular member 103.

Figure 9:
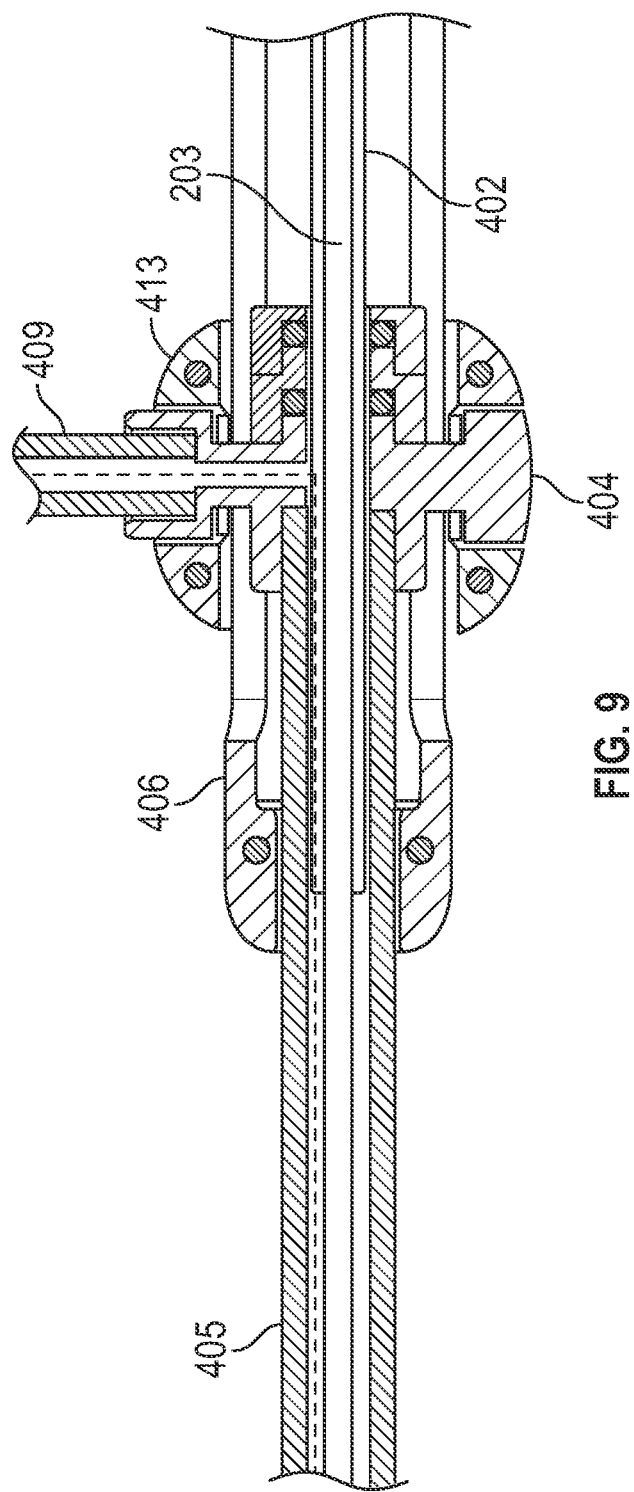
FIG. 9 is a cross sectional illustration showing a view of the control handle, where dashed lines depict a fluid flow path from a side port.

FIG. 9 is a cross-sectional illustration of the control handle assembly showing many of the same elements as FIG. 4. The following discussion is provided to summarize the operation of the tubular members and the control handle assembly as depicted in FIGS. 1, 2, 4 and 9. The key point is that the inner tubular member 203 is fixed relative to the control handle 105, while the outer tubular member 103 slides relative to the inner tubular member 203 based on movement of the control ring 109 along the control handle 105 (FIGS. 1 & 2). After assembly, the inner tubular member 203 is fixed in longitudinal position relative to the control handle 105, which is embodied primarily in the two halves of the control handle mechanism housing 406. The hypotube 402 supports the inner tubular member 203 to prevent kinking, and the luer 407 allows a fluidic coupling to the inside of the inner tubular member 203. The outer tubular member 103 slides longitudinally relative to the inner tubular member 203 and the control handle 105, driven by the position of the control ring 109, which is embodied primarily in the circular control ring halves 413 and the control ring main body 404. The flexible slider tube 405 transfers motion of the control ring 109 to the outer tubular member 103 itself. The flexible slider tube 405 slides over the hypotube 402 within the handle assembly. The annular space between the inner tubular member 203 and the outer tubular member 103 is in fluid communication with the side port tubing 409 and the side port 408, as shown in FIGS. 4 and 9.

FIG. 5a shows a depiction of an embodiment of the currently disclosed catheter system in an initial configuration and FIG. 5b shows the same catheter system in a second configuration. FIGS. 5-8 depict different embodiments than the figures discussed previously, where in particular, the embodiments of FIGS. 5-8 include handle features for locking the extension/retraction position of the outer tubular member 103 relative to the inner tubular member 203, but do not include a side port. FIGS. 5a/b include a control handle 605 and a control ring 603. As in earlier embodiments, longitudinal motion of the control ring 603 along the handle 605 moves the outer tubular member 103 relative to the inner tubular member 203. The position of the control ring 603 is shown in both an initial configuration (FIG. 5a, where the outer tubular member 103 is fully extended over and covers the inner tubular member 203) and a second configuration (FIG. 5b, where the control ring 603 and the outer tubular member 103 have been retracted, exposing the pigtail 205 at the distal end 206 of the inner tubular member 203). The position of the control ring 603 controls the exposed amount of the inner tubular member 203, which in turn correlates to the configuration of the catheter tip, thus providing a visual cue to the operator of the distal tip configuration.

FIG. 6 shows the control handle 605 detached from the catheter. In this embodiment of the control handle mechanism, the range of travel is dictated by a slot 601 in the handle housing. The slot 601 may include a locking feature, a slot segment 607 extending 90 degrees from the longitudinal travel slot 601, at the proximal and distal (not shown) extremes of travel to provide for a twist lock mechanism to immobilize the circular control ring 603 and thus preventing unwanted catheter tip shape changes.

FIG. 7 shows a control handle 705 which includes a spring-loaded detent system actuated by a depressible release button 703 that may provide additional means to lock the catheter into position. The button 703 is a control element which replaces the control ring 603 of FIG. 6, and the outer tubular member 103 is attached to the button 703 for adjustment of the position of the outer tubular member 103. The button 703, when pressed, may move along a slot 704. Releasing the button 703 locks the button 703 in place, which locks the position of the outer tubular member 103 relative to the inner tubular member 203.

FIG. 8 shows the handle 605 with undulations 801 on the outer surface of the control ring 603, rather than the knurled surface of FIG. 6, to enhance the grip of the operator. The arrows in FIG. 8 depict the longitudinal travel of the control ring 603 relative to the handle 605, and rotation of the control ring 603 into the slots 607 at either end of the range of travel.

The handle embodiments of FIGS. 6-8 are shown to illustrate the outer tubular member 103 adjustment and locking features. For the sake of clarity and simplicity, these handle embodiments are not shown with additional features such as the side port 113 and the luer 111 of FIG. 1—but the side port and luer features are equally applicable to any and all handle embodiments, including those of FIGS. 6-8.

FIGS. 10a-10e show the presently disclosed catheter system 101 in the human anatomy in various stages of insertion and the corresponding catheter configuration. FIG. 10a shows the catheter system 101 being inserted into an artery remote from the heart, such as in the upper leg. The lengths of the outer tubular member 103 and inner tubular member 203 discussed previously are suitable for the catheter system 101 to traverse an artery all the way up to and into the heart.

FIG. 10b shows the catheter system 101 near a stenotic aortic valve of the heart. The distal end 107 of the outer tubular member 103, in an AL1 configuration, is visible with a guide wire 1002 extending from the outer tubular member 103. In FIG. 10b, the catheter system 101 has been inserted through the vasculature up to the aortic valve of the heart, and the outer tubular member 103 is still fully covering the inner tubular member 203, corresponding to the position of the control ring 109 at the distal end of the control handle 105. The guide wire 1002 is next used to guide the catheter system 101 through (across) the aortic valve into the ventricle. A plurality of holes 1050 may be provided through the wall of the outer tubular member 103 near its distal end 107, where the holes 1050 facilitate improved fluid communication to the proximal (handle) end of the outer tubular member 103 and therefore better measurement of pressure and/or better flow of fluids through the catheter system 101.

FIG. 10c shows the catheter system 101 in the left ventricle. In this figure, the outer tubular member 103 is still fully covering the inner tubular member 203, as the position of the control ring 109 is still at the distal end of the control handle 105. The distal end 107 of the outer tubular member 103 remains in AL1 configuration and is now in its desired location in the ventricular chamber, where the holes 1050 facilitate blood pressure measurement by a sensor at the proximal end of the outer tubular member 103 (discussed below). FIG. 10c represents the stage in the procedure where the catheter system 101 has been inserted into position with the gently curved tip shape of the outer tubular member 103, the guide wire 1002 has been retracted, and the procedure involving the inner tubular member 203 is ready to begin.

FIG. 10d shows the catheter system 101 being transformed from an AL1 configuration to a pigtail configuration by beginning retraction of the outer tubular member 103. It can be seen in FIG. 10d that the control ring 109 has been moved over halfway toward the proximal end of the control handle 105, which causes the outer tubular member 103 to retract and expose part of the inner tubular member 203. The pigtail shape 205 is now visible at the distal end 206 of the inner tubular member 203. A plurality of holes 1060 may be provided through the wall of the inner tubular member 203 near its distal end 206, where the holes 1060 facilitate improved fluid communication to the proximal (handle) end of the inner tubular member 203 and therefore better measurement of pressure and/or better flow of fluids through the catheter system 101.

FIG. 10e shows the catheter system 101 with the outer tubular member 103 fully retracted back up above the aortic valve. It can be seen in FIG. 10e that the control ring 109 has been moved all the way to the proximal end of the control handle 105, which has caused the outer tubular member 103 to fully retract and expose a maximum amount of the inner tubular member 203. The holes 1050 in the outer tubular member 103 are visible above the aortic valve, where they improve fluid communication between the aortic location and the proximal end of the catheter system 101. The holes 1060 in the inner tubular member 203 are visible in the left ventricle, where they improve fluid communication between the ventricular location and the proximal end of the catheter system 101.

FIG. 10e also shows a pressure transducer 1012 mounted at the side port 113, and a pressure transducer 1022 mounted at the luer 111 to facilitate differential blood pressure measurements, and an inset showing the pressure measurement as it might appear on a viewing instrument. Recall that the luer 111 is in fluid communication with the inside of the inner tubular member 203, and the side port 113 is in fluid communication with the annular space between the outer tubular member 103 and the inner tubular member 203. Thus, the pressure transducer 1012 is measuring pressure at the tip of the outer tubular member 103 above the aortic valve, and the pressure transducer 1022 is measuring pressure at the tip of the inner tubular member 203 in the ventricular chamber. The transducer 1012 provides a signal to the display 1030 via wire 1014, and the transducer 1022 provides a signal to the display 1030 via wire 1024. Alternatively, the transducers may communicate wirelessly with the display and any related computer monitoring system.

FIG. 10e also shows a fluid tube 1010 passing through the pressure transducer 1012 and a fluid tube 1020 passing through the pressure transducer 1022. The fluid tube 1010 is connected to the side port 113 and could be used to introduce a fluid to or withdraw a fluid from the tip of the outer tubular member 103, which in this case is above the aortic valve. The fluid tube 1020 is connected to the luer 111 and could be used to introduce a fluid to or withdraw a fluid from the tip of the inner tubular member 203, which in this case is in the ventricular chamber. Techniques are used to prevent air embolization in the blood stream and air in the tubes 1010 and 1020.

Rather than the transducers 1012 and 1022 to measure blood pressure as shown in FIG. 10, the catheter system 101 may include a sensor mounted near the distal tip of the outer tubular member 103 and/or the inner tubular member 203 to monitor blood pressure (not shown).

The inner tubular member 203 is comprised of a relatively stiff proximal tubular member that is adapted for the outer tubular member 103 to slide over it and have sufficient column strength to avoid buckling. The proximal segment 221 of the inner tubular member 203 can be fused to a more flexible distal segment 222 by any number of means including heat or adhesive bonding. The proximal segment 221 of the inner tubular member 203 may be made of a braid reinforced polymer tubing capable of withstanding high internal pressures without failure. This facilitates the use of a pressure injection system for radiopaque contrast injection into the heart for imaging. The proximal segment 221 of the inner tubular member 203 may be made from a stiffer material such as 304 stainless steel or a reinforced polyimide tube. Alternatively, the inner tubular member proximal segment 221 could have a reinforcing sleeve to provide needed stiffness.

The diameter dimensions of the present technology at its proximal end, where it is reinforced or stiffened, can be different than the diameter dimensions, both inner and outer diameters, of the distal segment 222 that enters into the patient or body.

The outer tubular member 103 similarly has a relatively stiffer proximal segment 121 and a more flexible distal segment 122. The proximal segment 121 is designed to withstand buckling as it is advanced and retracted over the outer diameter of the inner tubular member 203. Similar to the inner tubular member 203, the inner and outer diameter dimensions of the distal segment 122 that enters into the body may differ from the portion that interacts with or is in the handle control mechanism.

The catheter system 101 may come in two lengths, such as a standard 100 cm, and a longer 125 cm catheter. Once the sterile catheter system is removed from the sterile packaging, a 150 cm J-tipped guide wire can be inserted into the catheter system 101 (through the interior of the inner tubular member 203) to allow placement of the catheter close to the aortic valve. Once in place, the 150 cm guide wire is removed and a standard 150 cm straight tipped guide wire is placed through the port or luer 111 attached to the base (proximal end) of the handle 105. This port or luer 111 can also enable measurement of left ventricular pressures as discussed above. This is accomplished by attaching an external pressure transducer to this port or, alternatively, incorporating a MEMS or optical pressure sensor into the catheter in fluid communication with the lumen connected to this port.

A second port, the sliding side port 113, is attached to the handle slide mechanism at the control ring 109 and is in fluid communication with the outer tubular member 103. This side port 113 enables the outer tubular member 103 to be flushed with sterile saline or other fluids through the lumen of the outer tubular member 103 (AL shaped catheter). This port also enables measurement of aortic pressures through the lumen of the outer tubular member 103 or AL shaped catheter. In yet another embodiment, additional side holes may be placed in the outer tubular member 103 to facilitate more accurate, or less damped, pressure measurements.

Another application of the present technology is for radial PCI. This embodiment provides a single device that can optimally and predictably be used in place of multiple devices for performing invasive radial angiography. The control handle mechanism converts the shape of the catheter distal tip from one shape to another to perform as a diagnostic catheter for angiography and then permit the outer tubular member 103 to be retracted to expose the inner tubular member 203 to perform contralateral vessel angiography. In this respect, the control handle mechanism is similar to the transcatheter aortic valve application, although the method of use may vary between procedures. Advantageously, this configuration enables an initial tip configuration to facilitate navigation through the body's vasculature system. When at the target location, then the tip can be transformed to a more aggressive shape, to more optimally perform the procedure in the coronary arteries. The more aggressive tip shape of the inner tubular member 203, which may be wildly contoured and capable of causing injury during delivery, is sheathed by an optimally shaped outer tubular member 103 until the device is advanced to the treatment zone. The risk of injury is reduced because an optimal shape is maintained during delivery.

An alternative embodiment for the present technology is for use in interventional cardiology procedures, such as PCIs, where devices are inserted into occluded coronary arteries to reopen them and to provide blood to the heart. In difficult cases, known in the field as complex PCI, extra support is often needed to prevent the guide catheter from backing out of the artery to be treated. In these situations where additional support is needed to deliver either a PTCA balloon or a coronary stent to the target lesion, the inner tubular member 203 is configured to be able to extend from within the outer tubular member 103 into the coronary arteries. The present technology enables this capability faster and easier than the current approach of using multiple devices that require exchanges. In this embodiment, the outer tubular member 103 would replace the function of a standard guide catheter, which typically is placed near the ostium of the vessel to be treated. The inner tubular member 203 is extended from the outer tubular member 103 and is then advanced into the coronary artery to provide extra support. In these procedures, frequent catheter manipulations, including rotating the device, makes it advantageous for the extended inner tubular member 203 to be collapsed so it resides inside the handle control mechanism. This eliminates the proximal segment from extending over the hands of the operator and flopping around during device manipulation.

The previously described control handle mechanism can be used in this application but the movement of the outer catheter would be in the opposite direction. The inner tubular member 203 is attached to and advanced by the control handle mechanism to extend past the outer tubular member 103. A handle embodiment may include provisions to enable a telescoping feature of the handle. This enables an original total catheter length (inner tubular member 203 and outer tubular member 103) that is desirably short for this procedure, for example 90 cm long. When utilizing the telescoping feature for the handle, the inner tubular member 203 assembly is configured so that the telescoping handle can be initially extended proximally (towards the operator and away from the patient); then, during the procedure, the telescoping sections of the handle can be collapsed, thus lengthening the inner tubular member 203 so it may be extended past the outer tubular member 103. In a fully extended position the device length can increase from 90 cm to 125 cm. There can be a means to limit the range of lengths of the inner tubular member 203.

The telescoping feature can be comprised of multiple tubular members designed to slide over each other in this handle embodiment. Each tubular member has a specified diameter that enables it to be slidably positioned over the underlying tubular member having a smaller diameter. There can be two such tubular members, which enable almost doubling the length of the telescoping component of the handle. Additionally, more than two tubular members may be employed in the same fashion to achieve a greater change in length. The distal most tip of the telescoping handle is attached to the proximal end of the catheter inner tubular member 203. The attachment provides for a sealed lumen preventing a leak path for air to enter into the body. A sealing means, such as O-rings, is used to ensure the telescoping handle mechanism is also sealed.

The present technology could be configured to have an inflatable balloon at its distal end to provide even more support. The balloon is attached to either the inner tubular member 203 or the outer tubular member 103. Two balloons, one attached to each tubular member, is also contemplated. It is also advantageous to incorporate a discrete radiopaque marker component at the distal end of one or both of the tubular members 103/203 so that the operator knows the position of the tip of the catheter system 101 in the arterial anatomy. A radiopaque marker may be made of platinum or a platinum alloy, such as 90% platinum and 10% iridium. There are other suitable radiopaque materials or alloys for this function.

The present technology may also have the inner tubular member 203 and the outer tubular member 103 loaded, or filled, with a dense radiopaque material to further improve visibility under fluoroscopy or x-ray systems. In this case, a material such as barium sulfate is added to the polymers which ultimately are extruded into tubular form. The ratio of the additive to the parent tubing material may be 80% tubing material and 20% radiopaque additive. Other ratios can be utilized to provide adequate imaging under fluoroscopy.

This embodiment of the present technology would also allow the use of a buddy wire system, which can be used for complex PCI. A buddy wire system is when an additional guide wire, is inserted along with the guide wire already in place, is employed through the guide catheter to help facilitate the procedure by providing extra stability or an anchoring function.

This particular embodiment would allow less imaging contrast to be used for complex PCI because there are fewer device exchanges and the inner tubular member 203 is of a smaller diameter lumen, which permits less contrast needed for visualization. Reducing the use of radiopaque contrast for imaging is beneficial to the patient and the hospital staff in the catheter lab.

The present technology simplifies currently practiced procedures by allowing for fewer catheter and guide wire exchanges, thereby reducing reducing risk associated with the procedure. Outlined below are methods utilizing the present technology.

FIG. 12 is a flowchart diagram 1200 of a method for employing the disclosed catheter system 101 shown in FIGS. 1-11. At box 1202, the catheter system 101 is advanced with a pre-shaped tip, such as an Amplatzer 1 or ALL through a puncture site into the vasculature, such as the femoral artery, of a patient and to a target site of interest in the body, such as the heart. The step at the box 1202, where the outer tubular member 103 fully covers the inner tubular member 203, is shown in FIG. 10a discussed previously. Once the device is brought close to the aortic valve through the arterial vasculature, at box 1204 the surgeon's left hand (usually index finger and thumb) is used to stabilize the device by holding the control handle mechanism. In addition, the left hand can gently rotate the catheter clockwise or counterclockwise in order to provide different angles for the distal end 107 of the device to cross the stenotic aortic valve. Using the right hand, a straight tipped guide wire 1002, inserted through the Amplatzer lumen, is gently advanced and retracted until it is across the aortic valve. FIG. 10b shows the actions of the box 1204.

Once the guide wire is across the aortic valve, at box 1206 the catheter system 101 is gently advanced into the left ventricle, the straight tipped guide wire 1002 is removed, and the proximal port 111 on the handle 105 is flushed with sterile saline solution. An external pressure transducer is then attached to the port 111 to make a pressure measurement. FIG. 10c shows the actions of the box 1206. At box 1208, holding the control handle 105 with the right hand, the left hand is moved to the handle sliding control ring 109. The right hand is in a fixed position (usually the entire right hand), and the left hand (index finger and thumb) pulls the control ring 109 proximally towards the right hand. Once the handle sliding control ring is fully moved towards the right hand, then the outer tubular member 103, for example the AL1 shaped catheter, is pulled back and exposes the inner tubular member 203, which can be shaped like a pigtail catheter. FIG. 10d shows the outer tubular member 103 partially retracted, and Figure shows the outer tubular member 103 fully retracted by the movement of the control ring 105 performed at the box 1208.

In this configuration, simultaneous pressure measurements can be made by attaching a second pressure transducer to the side port, which is done after appropriate flushing. For example, differential pressure readings between the left ventricle and aorta can be made by two external transducers, as described above, attached to each of the two ports on the present technology which interrogate each of the two lumens within the device, respectively. Each of the pressure transducers is interrogating separate places in the body, for example, in this case the left ventricle and the aorta. At box 1210, shown in FIG. 10e, the catheter system 101 is in position, with the inner tubular member 203 exposed and in position in the left ventricle, and pressure monitors operational. At this point, catheter placement has been completed and the patient procedure (such as a TAVR or a PCI) may be performed.

Using an alternative embodiment, shown in the handle 605 of FIGS. 6 and 8, once in the left ventricle, a control ring mechanism is rotated to unlock the inner tubular member 203 and outer tubular member 103 from a fixed relative position. The operator retracts the ring along a defined longitudinal length moving the ring from one extreme position to the opposite extreme position by moving the control ring mechanism. A hard physical stop prevents movement beyond the defined extreme positions. These two extreme positions of the control ring mechanism correlate with conversion of the catheter tip configuration from one preset shaped to a second preset shape, by retracting the outer tubular member 103 and exposing the inner tubular member 203 distal end. In the handle embodiment of FIG. 7, a push button is used to lock/unlock the control handle configuration.

In the methods discussed above according to this aspect of the present technology, the user desirably positions the device in an improved fashion within the left ventricle. The ability to use an initial tip configuration (of the outer tubular member 103) for advancement of the catheter system into the ventricle, and a second tip configuration (of the inner tubular member 203) during performance of the procedure once in place, provides protection against injury to the arteries or the heart wall. The method desirably further includes the step of completing this shape change without the operator having to look directly at the handle mechanism. Methods according to this aspect of the present technology afford advantages similar to those discussed above in connection with the apparatus.

In addition, this catheter can then be used for optimized and improved placement of the stiff wire for balloon valvuloplasty and transcatheter aortic valve replacement procedures. A stiff guide wire needed to appropriately stabilize and position the valvuloplasty balloon catheter can be inserted into presently disclosed inner tubular member 203 and positioned as desired. The operator would then remove the catheter system 101 while maintaining position of the stiff guide wire. Once the catheter system 101 is fully removed from the guide wire, a valvuloplasty balloon or transcatheter aortic valve can be inserted over the guide wire into position within the anatomy.

It is understood that the present technology with its quick catheter tip shape change capability can be applied to other applications that benefit from the need to reduce device exchanges or procedure time. For example, in radial PCI procedures, there is a desire to minimize device exchanges in delicate arteries in the arm. Radial procedures offer patient benefits over traditional femoral artery approaches, reduced recovery time, and fewer access site bleeding complications. Published clinical literature has shown mortality benefits using the radial access approach over the more traditional femoral artery approach. Consequently, the use of radial access PCI procedures have supplanted femoral artery PCI in many labs throughout the world. In addition, many other applications for the disclosed device are envisioned— including applications in the fields of neurology, urology, and peripheral vascular procedures.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of using a concentric two-tube catheter device including an inner tubular member and an outer tubular member, the method comprising:
    sliding the outer tubular member relative to the inner tubular member, via a sliding of a control element attached to the outer tubular member relative to a handle body of the catheter device attached to the inner tubular member, to expose a distal end of the inner tubular member from a distal end of the outer tubular member, the distal end of the outer tubular member providing a first shape, the distal end of the inner tubular member providing a second shape upon exposure thereof, wherein the first shape and the second shape are different;
    monitoring a first pressure at the distal end of the inner tubular member by way of a first flow path through the catheter device after sliding the outer tubular member relative to the inner tubular member to expose the distal end of the inner tubular member from the distal end of the outer tubular member, the first flow path including an interior of the inner tubular member;
    monitoring a second pressure at the distal end of the outer tubular member by way of a second flow path through the catheter device after sliding the outer tubular member relative to the inner tubular member to expose the distal end of the inner tubular member from the distal end of the outer tubular member, the second flow path including an opening formed through the control element from an outer surface thereof to an inner surface thereof and an annular space present between the inner tubular member and the outer tubular member.

2. The method of claim 1, wherein the first shape has less curvature than the second shape.

3. The method of claim 1, wherein the first shape has a shorter curved length than the second shape.

4. The method of claim 1, wherein the first shape includes one of an Amplatz shape and a Judkins shape.

5. The method of claim 1, wherein the second shape includes a pigtail shape.

6. The method of claim 1, wherein the second shape includes the distal end of the inner tubular member curving at least about 270 degrees from a remainder of the inner tubular member.

7. The method of claim 1, wherein the first shape includes a hook shape and the second shape includes a pigtail shape.

8. The method of claim 1, wherein the outer tubular member has a bending stiffness greater than a bending stiffness of the inner tubular member resulting in the second shape of the distal end of the inner tubular member conforming to the first shape of the distal end of the outer tubular member when the distal end of the inner tubular member is covered by the distal end of the outer tubular member.

9. The method of claim 1, wherein the sliding of the outer tubular member relative to the inner tubular member to expose the distal end of the inner tubular member from the distal end of the outer tubular member includes the control element sliding in a distal to proximal direction on the handle body to retract the outer tubular member relative to the inner tubular member.

10. The method of claim 1, further comprising locking the inner tubular member relative to the outer tubular member.

11. The method of claim 1, wherein prior to sliding the outer tubular member relative to the inner tubular member to expose the distal end of the inner tubular member from the distal end of the outer tubular member, the method includes extending a guide wire through the distal end of the inner tubular member.

12. The method of claim 1, further comprising a member selected from a group comprising: providing a fluid at the distal end of the inner tubular member by way of the first flow path; withdrawing a fluid at the distal end of the inner tubular member by way of the first flow path; providing a fluid at the distal end of the outer tubular member by way of the second flow path; withdrawing a fluid at the distal end of the outer tubular member by way of the second flow path; and combinations thereof.

13. The method of claim 1, further comprising a member selected from a group comprising: inflating a balloon at the distal end of the inner tubular member by way of the first flow path; inflating a balloon at the distal end of the outer tubular member by way of the second flow path; and combinations thereof.

14. The method of claim 1, wherein after sliding the outer tubular member relative to the inner tubular member to expose the distal end of the inner tubular member from the distal end of the outer tubular member, the method further comprises a member of a group consisting of: delivering and inflating a balloon using the catheter device; delivering a stent using the catheter device; and delivering a prosthetic valve using the catheter device.

15. A method of treating a heart of a patient using a concentric two-tube catheter device including an inner tubular member and an outer tubular member, the method comprising:
    advancing the catheter device through an artery to the heart of the patient;
    extending a guide wire through a distal end of the inner tubular member across an aortic valve of the heart of the patient;
    advancing the catheter device into a ventricle of the heart of the heart of the patient; and
    retracting the outer tubular member relative to the inner tubular member to expose a distal end of the inner tubular member from a distal end of the outer tubular member, the distal end of the outer tubular member providing a first shape, the distal end of the inner tubular member providing a second shape upon exposure thereof, wherein the first shape and the second shape are different,
    wherein the outer tubular member is attached to a control element and the inner tubular member is attached to a handle body of the catheter device, wherein the retracting of the outer tubular member relative to the inner tubular member to expose the distal end of the inner tubular member from the distal end of the outer tubular member includes the control element sliding relative to the handle body, wherein the catheter device defines a first flow path in fluid communication with the distal end of the inner tubular member and a second flow path in fluid communication with the distal end of the outer tubular member, wherein the first flow path includes an interior of the inner tubular member and the second flow path includes an opening extending through the control element from an outer surface thereof to an inner surface thereof and an annular space disposed between the inner tubular member and the outer tubular member, wherein the first flow path is fluidly separated from the second flow path following the retracting of the outer tubular member relative to the inner tubular member to expose the distal end of the inner tubular member from the distal end of the outer tubular member.

16. The method of claim 15, further comprising a member selected from a group comprising: monitoring a pressure at the distal end of the inner tubular member by way of the first flow path; monitoring a pressure at the distal end of the outer tubular member by way of the second flow path; providing a fluid at the distal end of the inner tubular member by way of the first flow path; withdrawing a fluid at the distal end of the inner tubular member by way of the first flow path; providing a fluid at the distal end of the outer tubular member by way of the second flow path; withdrawing a fluid at the distal end of the outer tubular member by way of the second flow path; inflating a balloon at the distal end of the inner tubular member by way of the first flow path; inflating a balloon at the distal end of the outer tubular member by way of the second flow path; delivering and inflating a balloon using the catheter device; delivering a stent using the catheter device; and delivering a prosthetic valve using the catheter device.

17. The method of claim 1, wherein the opening extends through the control element in a radial direction of the handle body.

18. A method of using a concentric two-tube catheter device including an inner tubular member and an outer tubular member, the method comprising:
  sliding the outer tubular member relative to the inner tubular member, via a sliding of a control element attached to the outer tubular member relative to a handle body of the catheter device attached to the inner tubular member, to expose a distal end of the inner tubular member from a distal end of the outer tubular member, the distal end of the outer tubular member providing a first shape, the distal end of the inner tubular member providing a second shape upon exposure thereof, wherein the first shape and the second shape are different;
  providing a first fluid to or withdrawing the first fluid from the distal end of the inner tubular member by way of a first flow path through the catheter device after sliding the outer tubular member relative to the inner tubular member to expose the distal end of the inner tubular member from the distal end of the outer tubular member, the first flow path including an interior of the inner tubular member;
  providing a second fluid to or withdrawing the second fluid from the distal end of the inner tubular member by way of a second flow path through the catheter device after sliding the outer tubular member relative to the inner tubular member to expose the distal end of the inner tubular member from the distal end of the outer tubular member, the second flow path including an opening formed through the control element from an outer surface thereof to an inner surface thereof and an annular space present between the inner tubular member and the outer tubular member.

19. The method of claim 18, further comprising a member selected from a group comprising: inflating a balloon at the distal end of the inner tubular member by way of the first flow path; inflating a balloon at the distal end of the outer tubular member by way of the second flow path; and combinations thereof.

* * * * *